United States Patent
Miyamoto et al.

(10) Patent No.: US 9,566,796 B2
(45) Date of Patent: Feb. 14, 2017

(54) LIQUID SUPPLY DEVICE AND LIQUID EJECTION DEVICE

(71) Applicant: SEIKO EPSON CORPORATION, Tokyo (JP)

(72) Inventors: Satoru Miyamoto, Matsumoto (JP); Sosuke Yamasaki, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 15/072,117

(22) Filed: Mar. 16, 2016

(65) Prior Publication Data
US 2016/0271965 A1 Sep. 22, 2016

(30) Foreign Application Priority Data

Mar. 18, 2015 (JP) ................................ 2015-054197
Dec. 2, 2015 (JP) ................................ 2015-235278

(51) Int. Cl.
*B41J 2/175* (2006.01)
*A61M 5/142* (2006.01)
*A61B 18/00* (2006.01)
*F04B 11/00* (2006.01)
*A61B 17/16* (2006.01)
*A61B 17/3203* (2006.01)

(52) U.S. Cl.
CPC ......... *B41J 2/17596* (2013.01); *A61M 5/1422* (2013.01); *A61B 17/1628* (2013.01); *A61B 17/1644* (2013.01); *A61B 17/3203* (2013.01); *A61B 2018/0091* (2013.01); *F04B 11/005* (2013.01)

(58) Field of Classification Search
None
See application file for complete search history.

(56) References Cited

U.S. PATENT DOCUMENTS

2014/0127037 A1* 5/2014 Uchida ................. F04B 11/005
417/53
2014/0134001 A1 5/2014 Uchida et al.

FOREIGN PATENT DOCUMENTS

JP 2014-95353 A 7/2014

* cited by examiner

*Primary Examiner* — Lisa M Solomon
(74) *Attorney, Agent, or Firm* — Maschoff Brennan

(57) ABSTRACT

A liquid supply device includes a pump tube that supplies a liquid to a handpiece intermittently ejecting the liquid and a tube pump that passes the pump tube to supply the liquid. An internal diameter of the pump tube is equal to or less than $\phi$ 1.0 mm.

18 Claims, 20 Drawing Sheets

LIQUID SUPPLY DEVICE AND LIQUID EJECTION DEVICE

BACKGROUND

1. Technical Field

The present invention relates to supply of a liquid.

2. Related Art

Devices which supply liquids to handpieces intermittently ejecting the liquids are known (see JP-A-2014-95353). The liquid supply device disclosed in JP-A-2014-95353 includes two plunger pumps. Pulsation of a liquid to be supplied is reduced by causing the two plunger pumps to alternately supply the liquid.

In the case of the technology of the foregoing related art, it takes some labor and time to perform maintenance of the plunger pumps. In particular, when the plunger pumps are used for medical treatment, problems particularly occur in cases in which exchange or sterilization is necessary.

SUMMARY

An advantage of some aspects of the invention is that a variation in pressure of a liquid to be supplied is suppressed with a mechanism for which maintenance is simple in consideration of the technology of the related art.

The invention can be implemented as the following forms.

An aspect of the invention provides a liquid supply device. The liquid supply device includes a pump tube that supplies a liquid to a handpiece intermittently ejecting the liquid and a tube pump that passes the pump tube to supply the liquid. An internal diameter of the pump tube is equal to or less than $\phi$ 1.0 mm. According to the aspect of the invention, pulsation of the liquid supplied to the handpiece can be suppressed. The internal diameter of the pump tube is thin (equal to or less than $\phi$ 1.0 mm). Therefore, even when the liquid is supplied at the same flow rate as a flow rate in the case in which the internal diameter of the pump tube is thick, the number of rotations of the tube pump can be increased. Therefore, the variation in the pressure on the downstream of the pump tube is suppressed. Maintenance of the pump tube and the tube pump is simple.

In the aspect of the invention, the internal diameter of the pump tube may be equal to or less than $\phi$ 0.8 mm. According to the aspect of the invention with this configuration, the variation in the pressure can be further suppressed.

In the aspect of the invention, the internal diameter of the pump tube may be equal to or less than $\phi$ 0.5 mm. According to the aspect of the invention with this configuration, the variation in the pressure can be further suppressed.

In the aspect of the invention, the internal diameter of the pump tube may be equal to or greater than $\phi$ 0.5 mm. According to the aspect of the invention with this configuration, since the number of rotations of the tube pump is not excessively increased to ensure a predetermined flow rate, durability of the tube pump is improved.

In the aspect of the invention, a roller frequency of the tube pump may be equal to or greater than 3.84 Hz. According to the aspect of the invention with this configuration, it is possible to ensure the flow rate even when the internal diameter of the pump tube is thin.

In the aspect of the invention, the roller frequency of the tube pump may be equal to or greater than 6.56 Hz. According to the aspect of the invention with this configuration, it is possible to ensure the flow rate even when the internal diameter of the pump tube is thin.

In the aspect of the invention, the roller frequency of the tube pump may be equal to or greater than 12.8 Hz. According to the aspect of the invention with this configuration, it is possible to ensure the flow rate even when the internal diameter of the pump tube is thin.

In the aspect of the invention, a wall thickness of the pump tube may be equal to or greater than 1.6 mm. According to the aspect of the invention with this configuration, when a roller coming into contact with the pump tube is switched, deformation of the pump tube is suppressed. Thus, a sudden reduction in the pressure on the downstream of the pump tube is suppressed.

In the aspect of the invention, the handpiece may be a surgical excising mechanism. A supply flow rate by the tube pump may be equal to or greater than 3 ml/min and equal to or less than 10 ml/min. According to the aspect of the invention with this configuration, it is possible to appropriately supply the flow rate in excising by the intermittent ejection of the liquid.

The invention can be implemented in other various forms. For example, a liquid ejection device including the handpiece and the liquid supply device can be implemented.

BRIEF DESCRIPTION OF THE DRAWINGS

The invention will be described with reference to the accompanying drawings, wherein like numbers reference like elements.

DESCRIPTION OF EXEMPLARY EMBODIMENTS

First, an ejection mechanism and a suction mechanism for a liquid will be described by describing an overall of a liquid ejection device 20 with reference to FIGS. 1 to 10.

Figure 1:
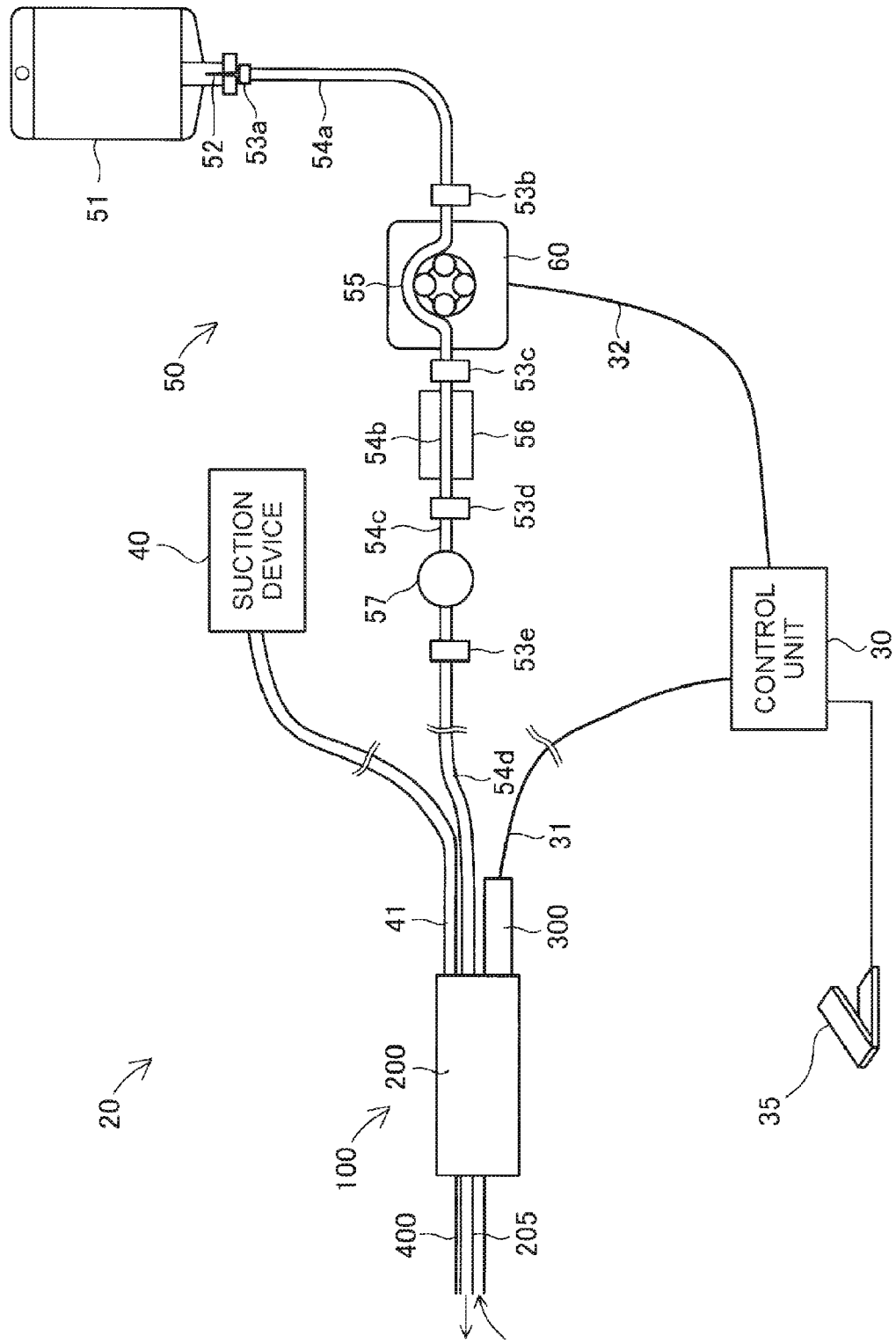
FIG. 1 is a diagram illustrating the schematic configuration of a liquid ejection device.

FIG. 1 schematically illustrates the configuration of the liquid ejection device 20. The liquid ejection device 20 is a medical apparatus used in a medical institution and has a function of excising a diseased part by ejecting a liquid to the diseased part.

The liquid ejection device 20 includes a control unit 30, an actuator cable 31, a pump cable 32, a foot switch 35, a suction device 40, a suction tube 41, a liquid supply device 50, and a handpiece 100 (operation unit).

The liquid supply device 50 includes a water feed bag 51, a spike needle 52, a first connector 53a to a fifth connector 53e, a first water feed tube 54a to a fourth water feed tube 54d, a pump tube 55, a blockade detection mechanism 56, and a filter 57. The handpiece 100 includes a nozzle unit 200 and an actuator unit 300. The nozzle unit 200 includes an ejection tube 205 and a suction tube 400.

The water feed bag 51 is made of a transparent synthetic resin and is filled internally with a liquid (specifically, a physiological salt solution). In the present specification, a bag filled with a liquid other than water is also referred to as the water feed bag 51. The spike needle 52 is connected to the first water feed tube 54a via the first connector 53a. When the spike needle 52 is punctured into the water feed bag 51, the liquid with which the water feed bag 51 is filled can be supplied to the first water feed tube 54a.

The first water feed tube 54a is connected to the pump tube 55 via the second connector 53b. The pump tube 55 is connected to the second water feed tube 54b via the third connector 53c. In the tube pump 60, the pump tube 55 is interposed between a stator and a rotor. The tube pump 60 passes (thrusts) the pump tube 55 by rotating a plurality of rollers through rotation of an internal motor. Bypassing the pump tube 55, the liquid inside the pump tube 55 is sent from the side of the first water feed tube 54a to the side of the second water feed tube 54b.

The blockade detection mechanism 56 detects a blockade inside the first water feed tube 54a to the fourth water feed tube 54d by measuring pressure inside the second water feed tube 54b.

The second water feed tube 54b is connected to the third water feed tube 54c via the fourth connector 53d. The filter 57 is connected to the third water feed tube 54c. The filter 57 captures foreign matters contained in the liquid.

The third water feed tube 54c is connected to the fourth water feed tube 54d via the fifth connector 53e. The fourth water feed tube 54d is connected to the handpiece 100. The liquid supplied to the handpiece 100 via the fourth water feed tube 54d is intermittently ejected from a nozzle 207 formed at the leading end of the ejection tube 205 through the driving of the actuator unit 300. By intermittently ejecting the liquid in this way, it is possible to ensure an excising capacity at a small flow rate.

The ejection tube 205 and the suction tube 400 are configured as double tubes in which the ejection tube 205 is an internal tube and the suction tube 400 is an external tube. The suction tube 41 is connected to the nozzle unit 200. The suction device 40 sucks the inside of the suction tube 400 via the suction tube 41. Through the suction, the liquid or excised pieces near the leading end of the suction tube 400 are sucked.

The control unit 30 controls the tube pump 60 and the actuator unit 300. Specifically, the control unit 30 transmits a drive signal via the actuator cable 31 and the pump cable 32 while the foot switch 35 is stepped on. The drive signal transmitted via the actuator cable 31 drives the actuator unit 300. The drive signal transmitted via the pump cable 32 drives the tube pump 60. Accordingly, while a user steps on the foot switch 35, the liquid is intermittently ejected. While the user does not step on the foot switch 35, the ejection of the liquid is stopped.

Figure 2:
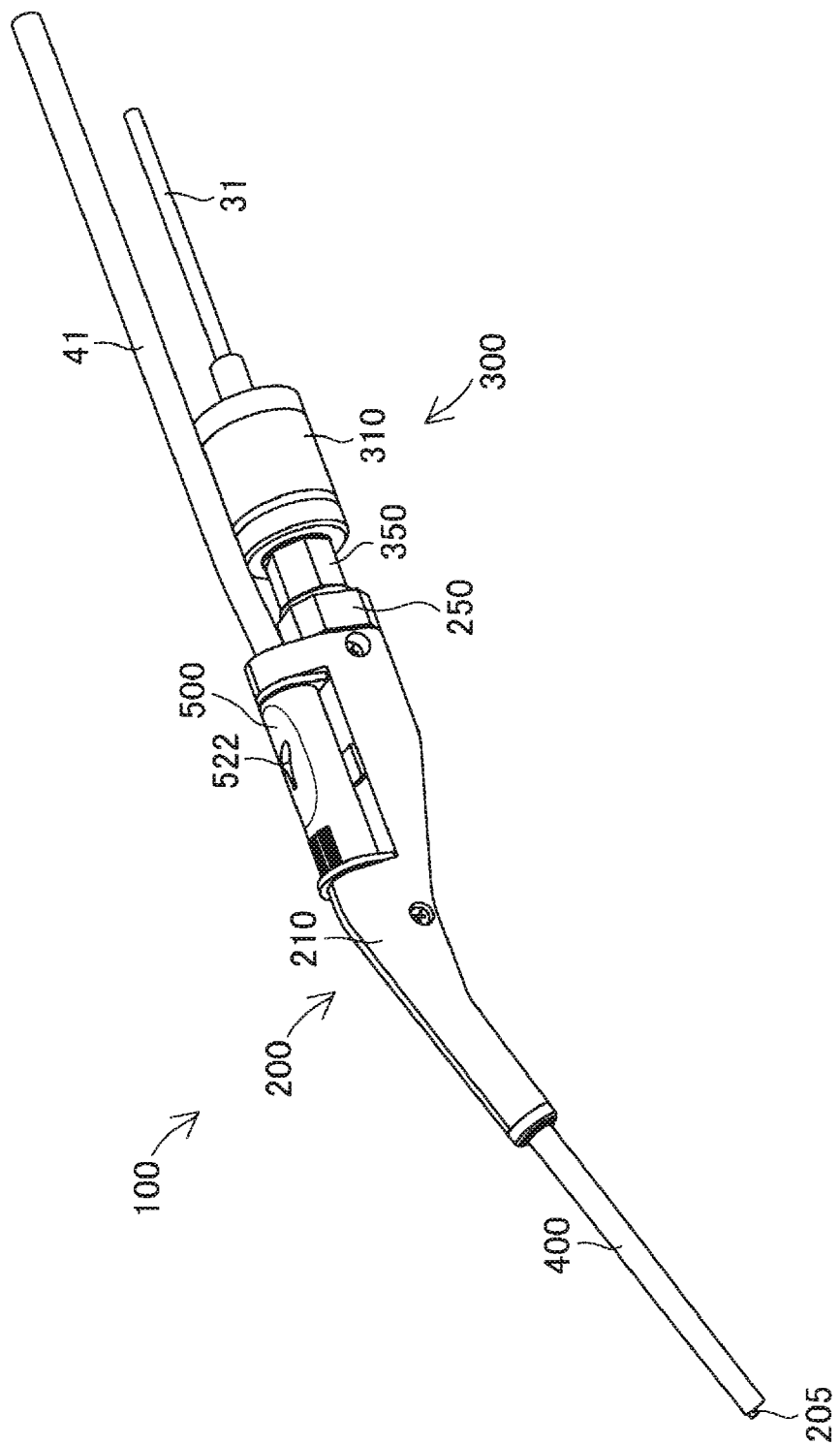
FIG. 2 is a perspective view illustrating a handpiece (fitted state).
Figure 3:
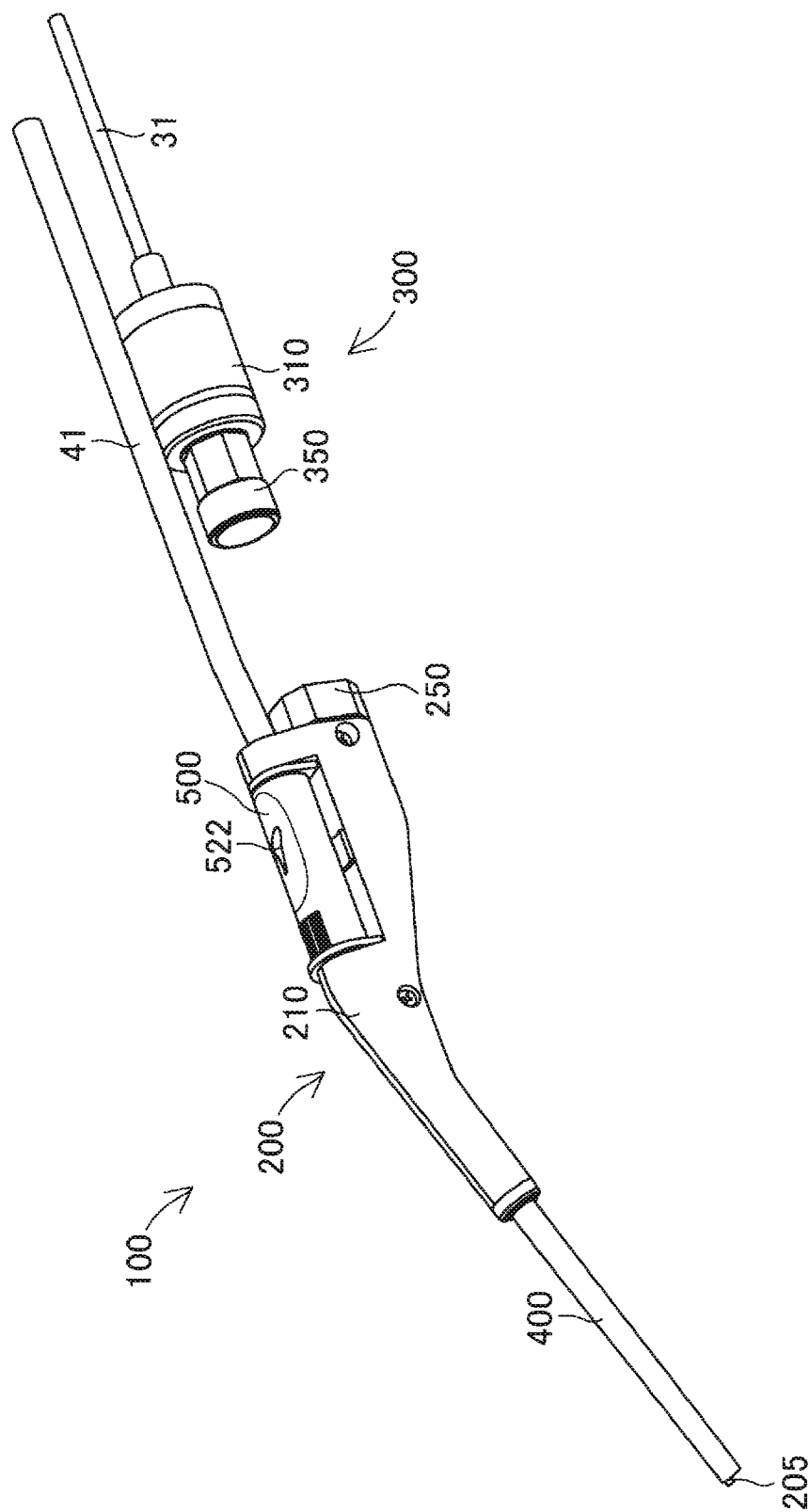
FIG. 3 is a perspective view illustrating the handpiece (separated state).

FIGS. 2 and 3 are perspective views illustrating the handpiece 100. FIG. 2 illustrates a state in which the actuator unit 300 is fitted to the nozzle unit 200 (hereinafter referred to as a "fitted state"). FIG. 3 illustrates a state in which the actuator unit 300 is separated from the nozzle unit 200 (hereinafter referred to as a "separated state").

The actuator unit 300 is configured to be detachably fitted to the nozzle unit 200. The actuator unit 300 is fitted to the nozzle unit 200 so that the actuator unit 300 and the nozzle unit 200 are integrated, and thus functions as the handpiece 100.

The liquid flows inside the nozzle unit 200, and thus the nozzle unit 200 is exchanged at each surgical operation. Of the constituent elements included in the liquid supply device 50, the constituent elements (the water feed bag 51, the first water feed tube 54a to the fourth water feed tube 54d, the pump tube 55, and the like) in which the liquid flows are exchanged at each surgical operation. Since the actuator unit 300 does not come into contact with the liquid, the actuator unit 300 can be used in a plurality of surgical operations by performing a sterilization treatment or a cleaning treatment.

The nozzle unit 200 includes a handpiece case 210, a joint portion 250, and a suction force adjustment mechanism 500 in addition to the ejection tube 205 and the suction tube 400 described above. The handpiece case 210 functions as a grip held by the user and has a function to maintain a channel internally. The channel is a channel along which the liquid to be ejected and the liquid to be sucked flow, as described above.

The suction force adjustment mechanism 500 is formed in the handpiece 100 and has a hole 522. When an open area of the hole 522 is changed, a suction force by the suction tube 400 is also changed (which will be described in detail with reference to FIG. 5). The joint portion 250 is a portion for detaching and fitting the actuator unit 300 from and to the nozzle unit 200.

The actuator unit 300 includes a connection portion 310 and a driving portion 350. The connection portion 310 mechanically and electrically connects the actuator cable 31 to the driving portion 350. The driving unit 350 generates a driving force to intermittently eject the liquid.

Figure 4:
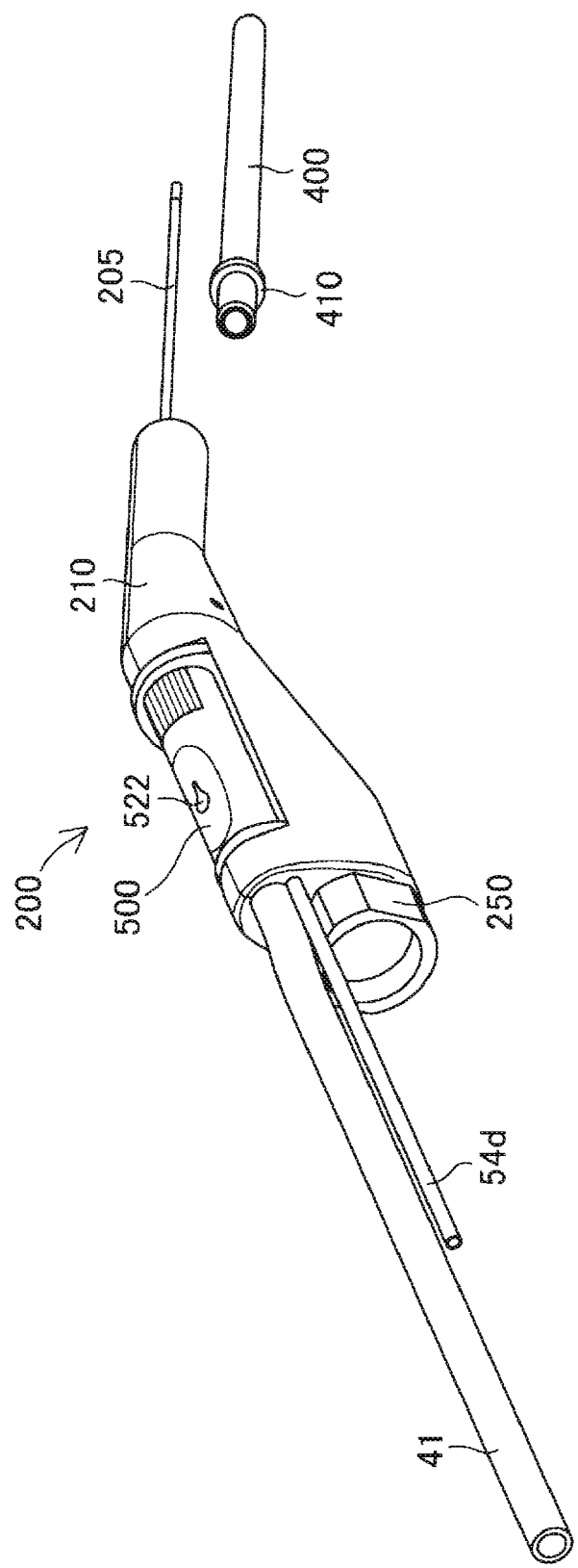
FIG. 4 is a perspective view illustrating a nozzle unit.

FIG. 4 is a perspective view illustrating the nozzle unit 200. FIG. 4 illustrates a state in which the suction tube 400 is detached from the handpiece case 210. The handpiece 100 may be used in the state in which the suction tube 400 is detached. In the state in which the suction tube 400 is detached, no suction can be performed using the suction tube 400, but the liquid can be ejected from the ejection tube 205.

The suction tube 400 includes a convex portion 410. The convex portion 410 is a portion that fits the suction tube 400 to the handpiece case 210.

As illustrated with reference to FIG. 1, the fourth water feed tube 54d is connected to the handpiece case 210. In FIGS. 2 and 3, the fourth water feed tube 54d is not illustrated due to visual perspective.

Figure 5:
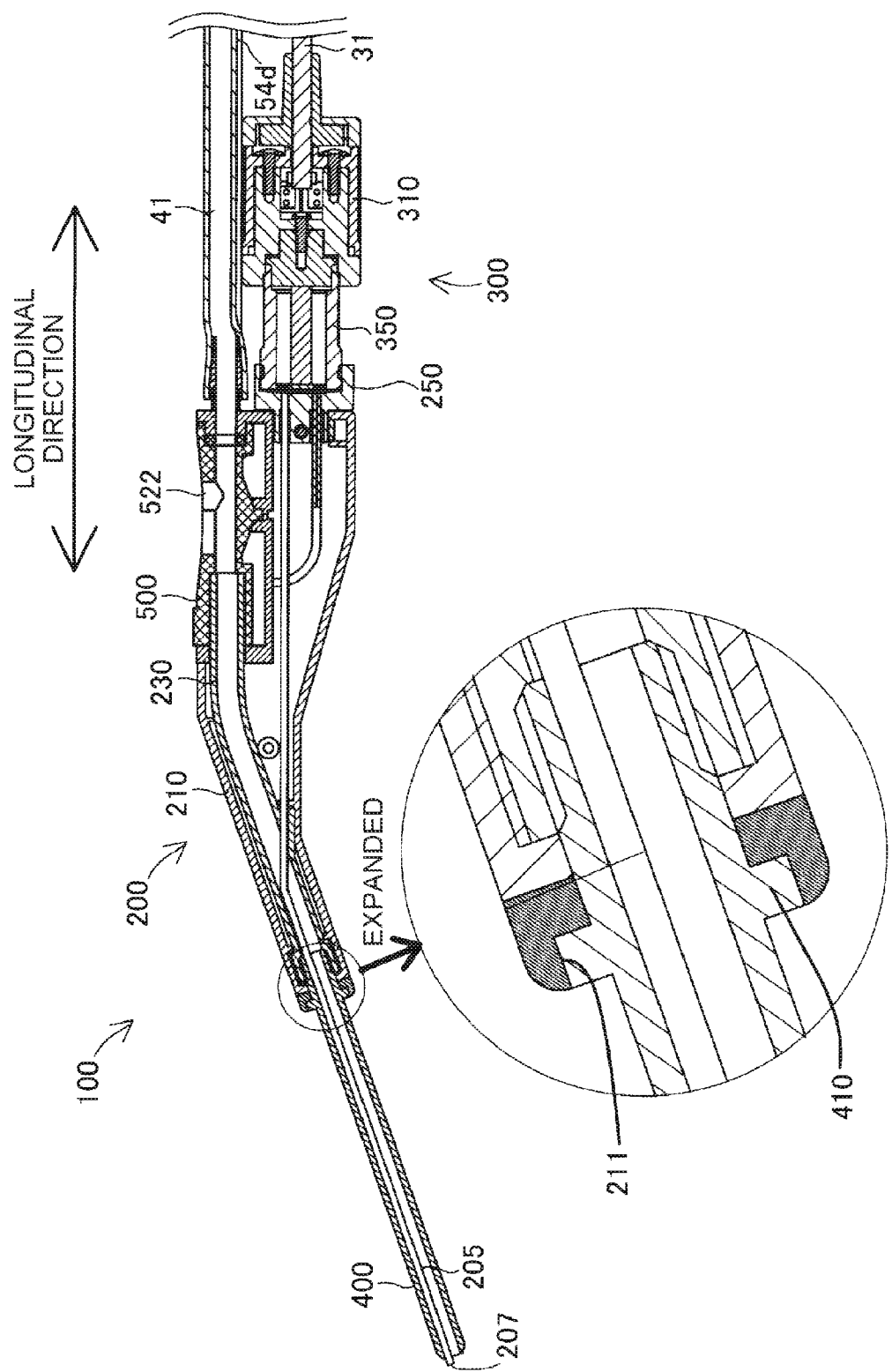
FIG. 5 is a sectional view illustrating the handpiece.

FIG. 5 is a sectional view illustrating the handpiece 100. The fourth water feed tube 54d is bent in a U shape inside the handpiece case 210 to be connected to an inlet channel 241. The inlet channel 241 communicates with the ejection tube 205 via a liquid chamber 240 (see FIGS. 8 and 9).

The channel diameter of the inlet channel 241 is less than the channel diameter of the ejection tube 205. Therefore, even when pressure varies inside the liquid chamber 240 (which will be described below), the liquid inside the liquid chamber 240 is prevented from flowing backward into the inlet channel 241.

The handpiece case 210 includes a concave portion 211 at the leading end. The fitting of the suction tube 400 is realized by engaging the convex portion 410 with the concave portion 211. The fitted suction tube 400 communicates with a suction channel portion 230. The suction channel portion 230 is connected to the suction tube 41 via the suction force adjustment mechanism 500.

The user can adjust a suction force by the suction tube 400 using the hole 522. Specifically, when an open area of the hole 522 is small, the flow rate of the air flowing from the hole 522 is small. Therefore, the flow rate of a fluid (the air, the liquid, or the like) sucked via the suction tube 400 increases. That is, the suction force by the suction tube 400 increases. In contrast, when the open area of the hole 522 is large, the flow rate of the air flowing from the hole 522 is large. Therefore, the suction force by the suction tube 400 decreases. Normally, the user realizes adjustment of the open area of the hole 522 by adjusting the area of the hole 522 blocked by his or her thumb. When the hole 522 is not covered at all, the shape of the hole 522 is designed so that the suction force by the suction tube 400 is minute or the suction force does not work. In the embodiment, the flow channel area of the suction tube 400 is greater than the open area of the hole 522. However, by causing the length of the suction tube 400 to be greater than the length of the hole 522, channel resistance of the suction tube 400 is configured to be greater than channel resistance of the hole 522. In this way, when the hole 522 is not covered at all, the suction force by the suction tube 400 can be minute.

As illustrated in FIG. 5, the longitudinal direction of the handpiece case 210 is defined. The longitudinal direction is a direction included in the cross section illustrated FIG. 5 and a horizontal direction at the time of a predetermined posture. The predetermined posture is a posture at which the user holds the handpiece 100 with his or her hand of which the palm is oriented upward. The longitudinal direction according to the embodiment is identical to a channel direction of the suction channel portion 230. The channel direction of the suction channel portion 230 is a direction of a flow inside the suction channel portion 230 in a portion of the suction channel portion 230 coming into contact with the suction force adjustment mechanism 500.

Figure 6:
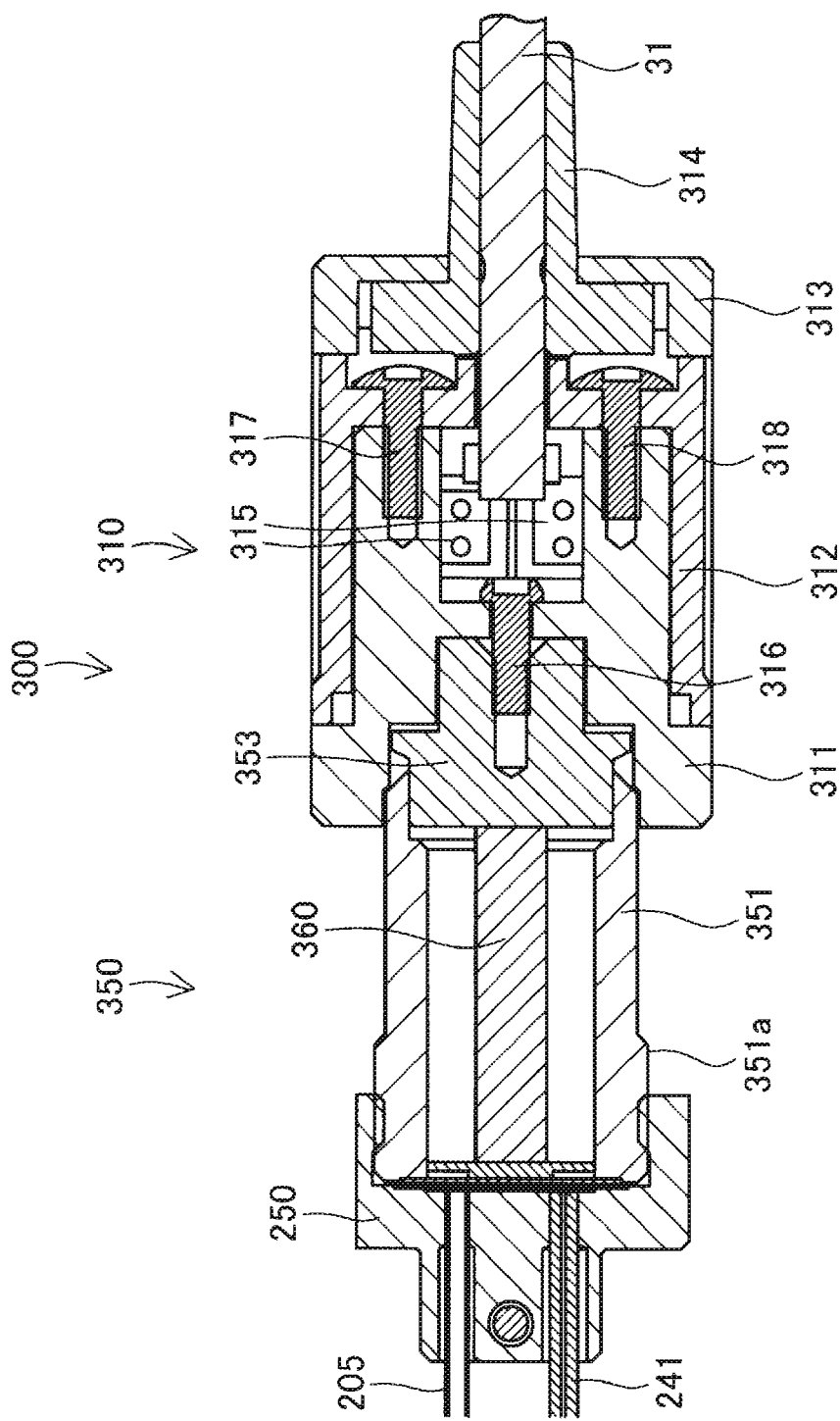
FIG. 6 is an expanded sectional view illustrating a joint portion and an actuator unit (fitted state).
Figure 7:
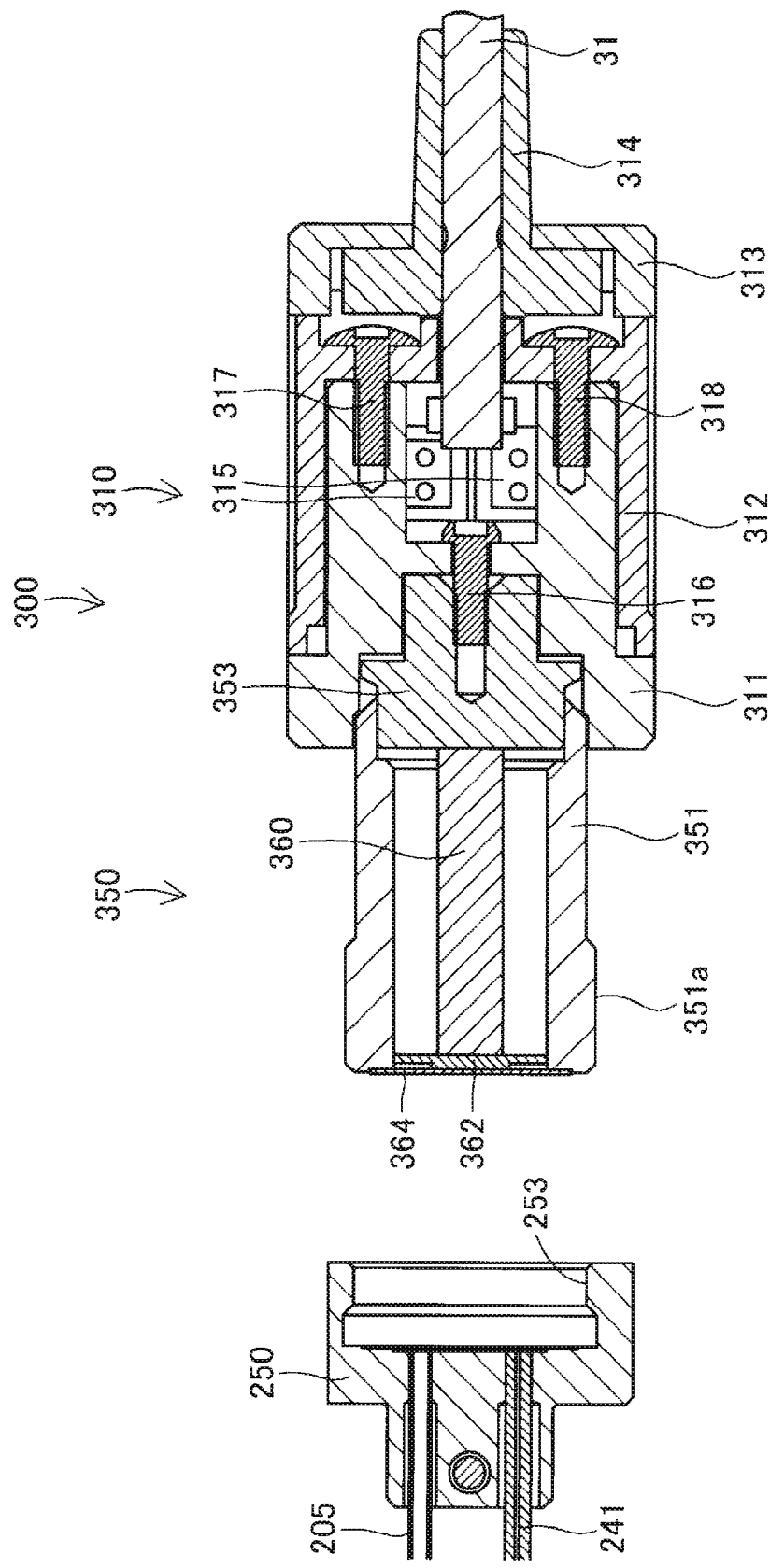
FIG. 7 is an expanded sectional view illustrating the joint portion and the actuator unit (separated state).

FIGS. 6 and 7 are expanded sectional views illustrating the vicinities of the joint portion 250 and the actuator unit 300. FIG. 6 illustrates a fitted state. FIG. 7 illustrates a separated state.

The driving portion 350 includes a housing 351, a fixed member 353, a piezoelectric element 360, and a movable plate 361. The housing 351 is a cylindrical member. The movable plate 361 includes a piston 362 and a driving side diaphragm 364.

The piezoelectric element 360 is a stacked piezoelectric element. The piezoelectric element 360 is disposed inside the housing 351 so that an expansion or contraction direction is parallel to the longitudinal direction of the housing 351. The piezoelectric element 360 according to the embodiment has a substantially right quadrangular prism shape with four sides of 3.5 mm and a height of 18 mm.

The fixed member 353 is fixed to one end of the housing 351. The piezoelectric element 360 is fixed to the fixed member 353 by an adhesive.

The material of the driving side diaphragm 364 is metal, specifically is stainless steel, and more specifically is SUS304 or SUS316L. The driving side diaphragm 364 has a thick form (for example, 300 μm) to perform preload (which will be described below) of the piezoelectric element 360. The piezoelectric element 360 is made of metal and the thick form. Therefore, when the piezoelectric element 360 is pushed by the piston 362, the piezoelectric element 360 is bent smoothly. Therefore, in the fitted state, a liquid chamber side diaphragm 260 can also be deformed smoothly.

The driving side diaphragm 364 is disposed to cover the other end of the housing 351 to be fixed to the housing 351 by welding.

The piston 362 is fixed to one end of the piezoelectric element 360 by an adhesive and is disposed to come into contact with the driving side diaphragm 364. The piston 362 has a shape in which columns with different diameters are stacked concentrically. The column with a small diameter comes into contact with the driving side diaphragm 364. Therefore, the end side of the driving side diaphragm 364 is not pushed and a large force is configured not to be applied to the welded portion. The piston 362 and the driving side diaphragm 364 merely come into contact with each other without being fixed by an adhesive or the like.

A male screw 351a is formed on the outer circumference of the housing 351. Transition from the separated state to the fitted state is realized by tightening the male screw 351a to a female screw 253 formed in the joint portion 250.

The connection portion 310 includes a first case 311, a second case 312, a third case 313, a hold member 314, metal plates 315, a first screw 316, a second screw 317, and a third screw 318. The metal plate 315 can also be restated as a relay substrate 315.

The first case 311 is fixed to the fixed member 353 by the first screw 316. The second case 312 is fixed to the first case 311 by the second screw 317 and the third screw 318. Two metal plates 315 are inserted (accommodated) inside the first case 311.

The hold member 314 is fastened to the vicinity of an end of the actuator cable 31 to be fixed. The third case 313 is a member which connects the second case 312 to the hold member 314. The third case 313 is locked in a portion in which the outer diameter of the hold member 314 is swollen, to be fixed to the second case 312.

In the foregoing fixed state, the actuator cable 31 is connected to be conductive with the two metal plates 315. The metal plates 315 are connected to positive and negative electrodes of the piezoelectric element 360 by wirings (not illustrated).

The piezoelectric element 360 is extracted or contracted according to a drive signal input via the actuator cable 31, the metal plates 315, and the wirings. When the piezoelectric element 360 is extracted or contracted, the piston 362 is vibrated in the longitudinal direction of the piezoelectric element 360. When the piston 362 is vibrated, the driving side diaphragm 364 follows the vibration to be deformed.

The piezoelectric element 360 is assembled in a preloaded state to appropriately perform the expansion or contraction. The preloaded state is a state in which the piezoelectric element 360 is pushed against the driving side diaphragm 364 and the piezoelectric element 360 is compressed in the expansion or contraction direction. A load of the preload is in the range of 10% to 50% of a maximum generation force of the piezoelectric element 360 and is specifically in the range of 40 N to 200 N. Therefore, even when no drive signal is input to the piezoelectric element 360, the driving side diaphragm 364 receives a force from the piezoelectric element 360 via the piston 362. The reason why the driving side diaphragm 364 is made of metal and is formed to be thicker than the liquid chamber side diaphragm 260 is to maintain the preload.

The driving side diaphragm 364 is deformed in the above-described manner. Therefore, even when the driving side diaphragm 364 is not attached to the piston 362, the driving side diaphragm 364 follows the contraction of the piezoelectric element 360 to be deformed.

Figure 8:
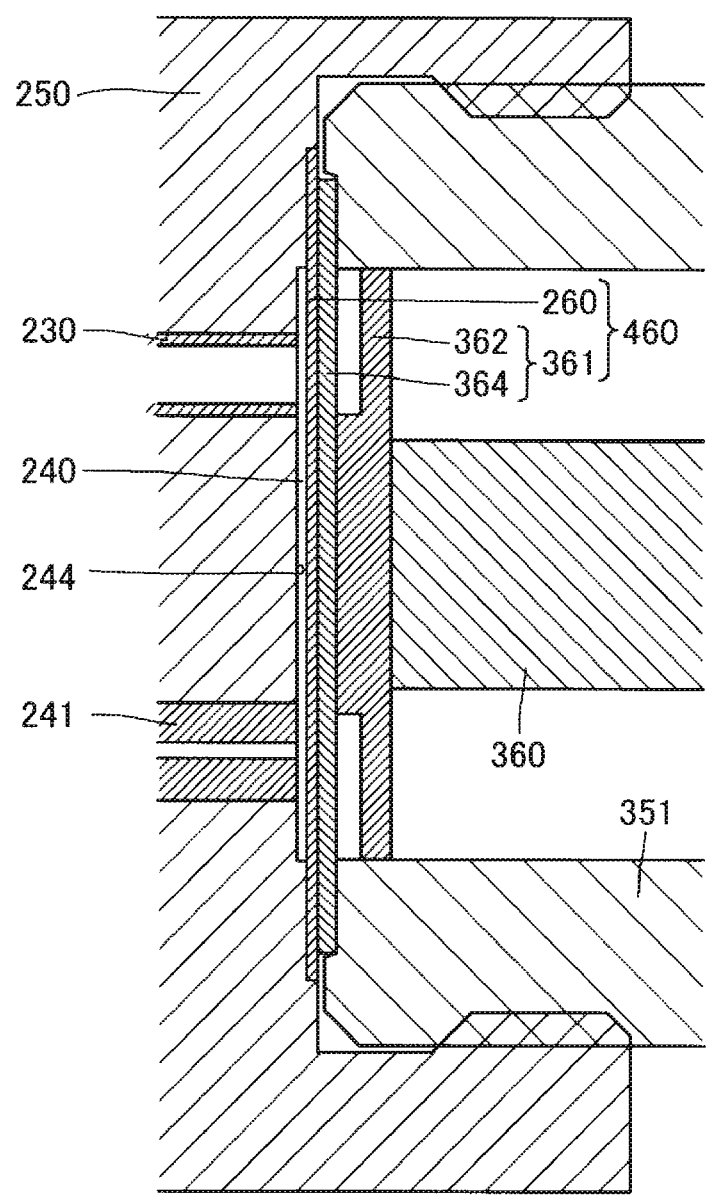
FIG. 8 is an expanded sectional view of the vicinity of a liquid chamber (fitted state).
Figure 9:
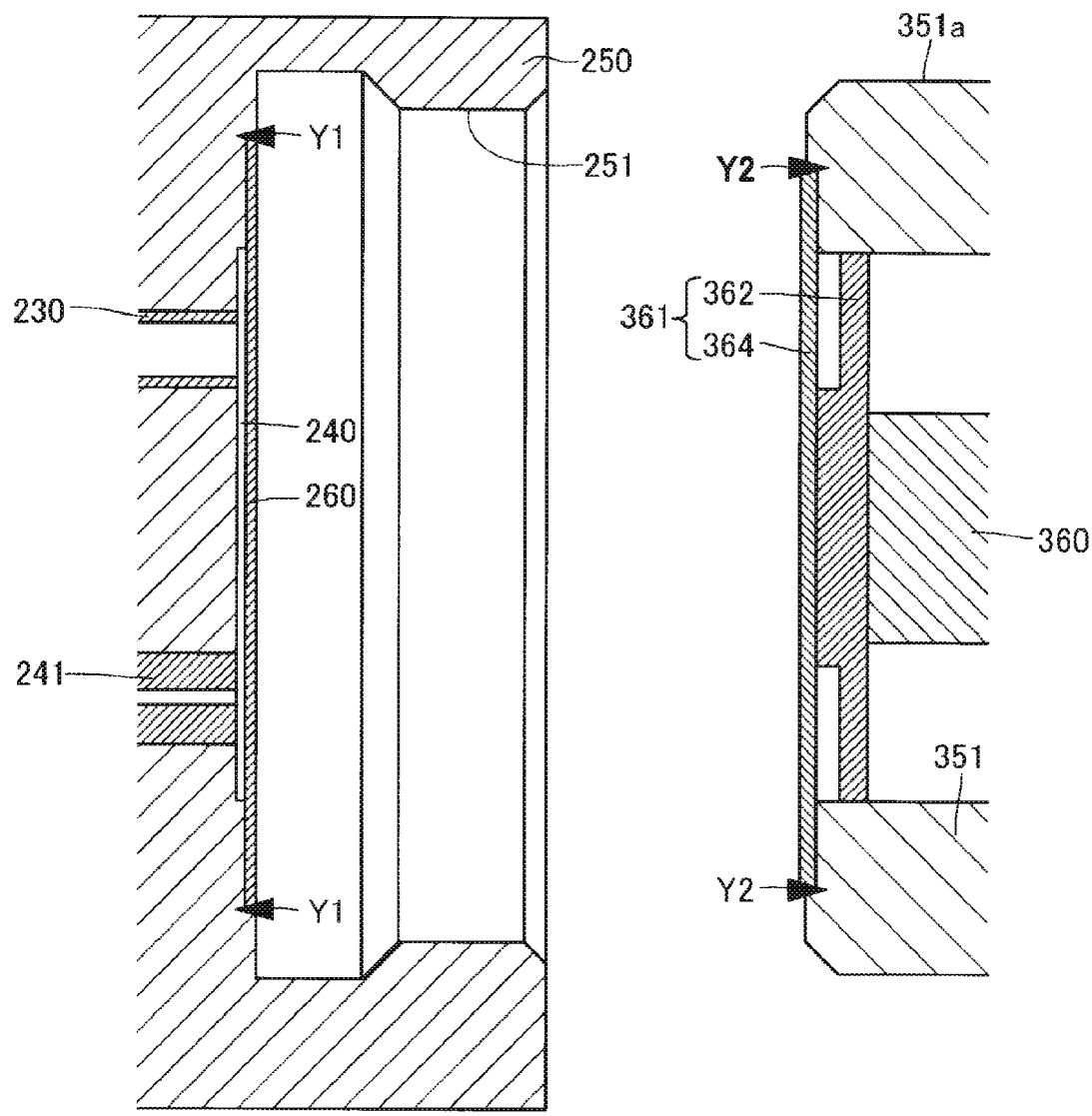
FIG. 9 is an expanded sectional view of the vicinity of the liquid chamber (separated state).

FIGS. 8 and 9 are expanded sectional views illustrating the vicinity of the liquid chamber 240. FIG. 8 illustrates a fitted state. FIG. 9 illustrates a separated state.

The liquid chamber 240 is formed inside the joint portion 250. The liquid chamber 240 is formed in a hollow 244 by covering the liquid chamber side diaphragm 260. The hollow 244 is a portion hollowed in a thin circular shape in the joint portion 250. The liquid chamber side diaphragm 260 is formed to be thinner than the driving side diaphragm 364 (for example, 50 μm to 100 μm) so that the liquid chamber side diaphragm 260 is easily deformed according to the expansion or contraction of the piezoelectric element 360. The diameter of the liquid chamber side diaphragm 260 is in the range of 13 mm to 15 mm. The liquid chamber side diaphragm 260 is fixed to the joint portion 250 by welding. The welded positions are illustrated as welds Y1 in FIG. 9. The material of the liquid chamber side diaphragm 260 is metal, specifically is stainless steel, and more specifically is SUS304 or SUS316L.

As illustrated in FIG. 8, the liquid chamber side diaphragm 260 and the driving side diaphragm 364 come into contact with each other in the fitted state. Therefore, as described above, when the driving side diaphragm 364 is deformed, the liquid chamber side diaphragm 260 is also deformed similarly.

When the driving side diaphragm 364 is deformed, the volume of the liquid chamber 240 varies. Due to this variation, the pressure of the liquid with which the liquid chamber 240 is filled varies. When the pressure inside the liquid chamber 240 decreases, the liquid flows into the liquid chamber 240 from the inlet channel 241. When the pressure inside the liquid chamber 240 increases, the liquid flows out to the ejection tube 205 from the liquid chamber 240. The liquid flowing out to the ejection tube 205 is ejected from the leading end of the ejection tube 205. Since the pressure inside the liquid chamber 240 intermittently increases, the liquid is intermittently ejected from the ejection tube 205.

In this way, the liquid chamber side diaphragm 260 and the driving side diaphragm 364 are integrated to be deformed. That is, the liquid chamber side diaphragm 260 and the movable plate 361 are integrated to be deformed. Reference numeral 460 illustrated in FIG. 8 denotes a combined diaphragm 460 in which the liquid chamber side diaphragm 260 and the movable plate 361 integrated to be deformed are combined. The combined diaphragm 460 can be comprehended as a single diaphragm in the fitted state.

Figure 10:
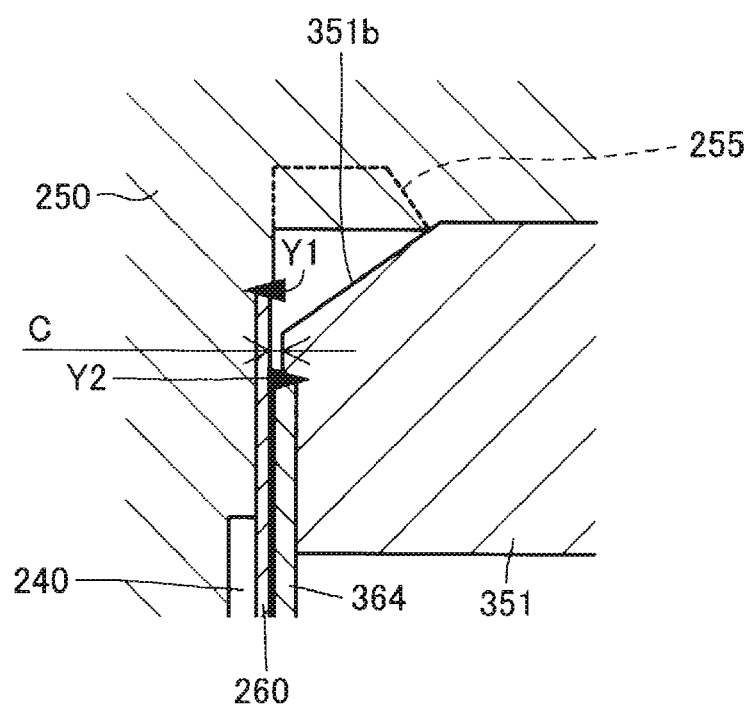
FIG. 10 is a diagram illustrating welding of a liquid chamber side diaphragm and a driving side diaphragm.

FIG. 10 is a diagram illustrating welding of the liquid chamber side diaphragm 260 and the driving side diaphragm 364. In the housing 351, a chamfered portion 351b is formed, as illustrated in FIG. 10. The chamfered portion 351b is formed so that the welds Y1 fixing the liquid chamber side diaphragm 260 and the housing 351 are not interfered with each other.

As illustrated in FIG. 10, the leading end of the housing 351 is further recessed by a size C than the leading end of the driving side diaphragm 364. As a result in the fitted state, a clearance occurs between the liquid chamber side diaphragm 260 and the housing 351. By performing welding so that a welding mark of a weld Y2 fixing the driving side diaphragm 364 is located at the clearance, it is possible to avoid interference between the weld Y2 and the liquid chamber side diaphragm 260.

Reference numeral 255 illustrated in FIG. 10 denotes a relief portion 255 in another form. In the embodiment, as illustrated in FIGS. 8 and 9 and the like, the relief portion 255 is not formed. The relief portion 255 is a portion in which a wall is recessed inward in the inner circumference of the joint portion 250. By forming the relief portion 255, the female screw 253 is easily processed.

Hereinafter, an influence of the inner diameter of the pump tube 55 will be described.

Figure 11:
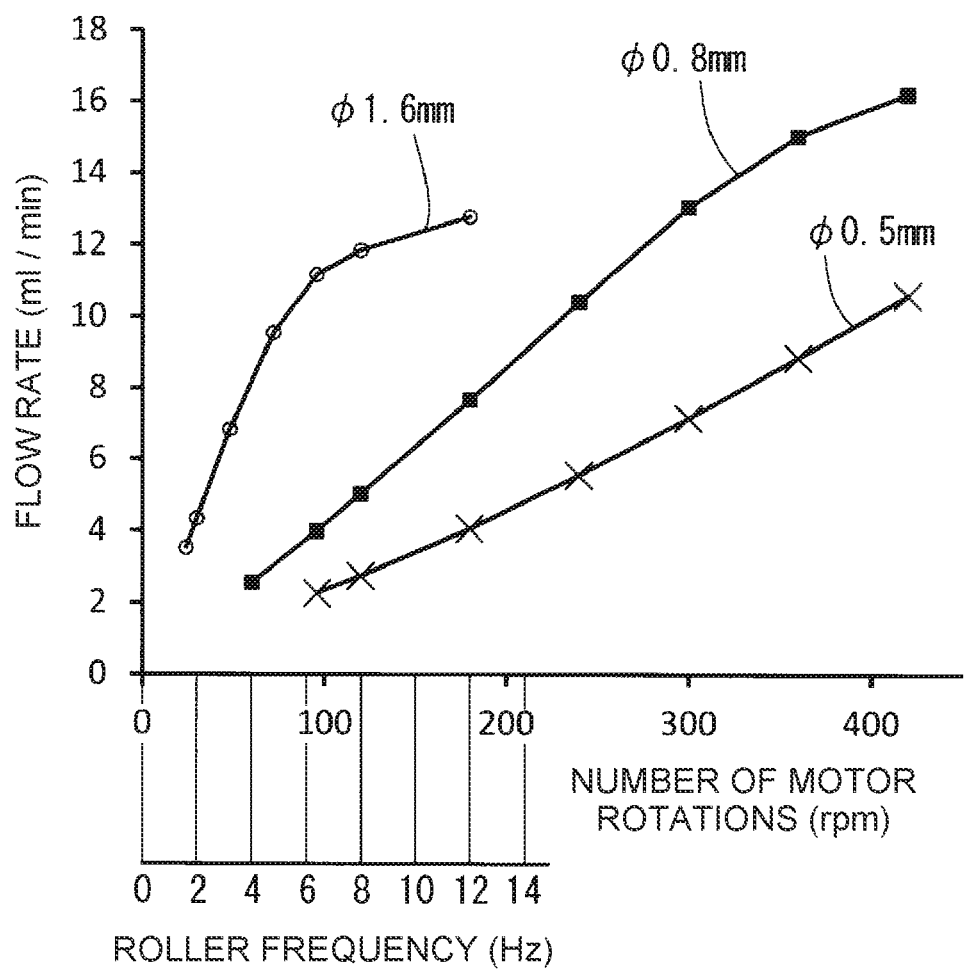
FIG. 11 is a graph illustrating a relation between a flow rate and the number of motor rotations.

FIG. 11 is a graph illustrating a relation of a flow rate (ml/min) of the liquid and the number of motor rotations (rpm) of the tube pump 60. FIG. 11 illustrates a case in which the internal diameter of the pump tube 55 is ϕ 1.6 mm, a case in which the internal diameter thereof is ϕ 0.8 mm, and a case in which the internal diameter thereof is ϕ 0.5 mm.

The wall thickness of the pump tube 55 according to the embodiment is 1.6 mm in any of the cases of the internal diameter. By causing the wall thickness of the pump tube 55 to be thick (1.6 mm), deformation is suppressed due to a sudden variation in pressure inside the pump tube 55. The sudden variation in the pressure inside the pump tube 55 occurs, for example, when the roller coming into contact with the pump tube 55 is switched.

Since the tube pump 60 according to the embodiment includes four rollers, a roller frequency is four times the frequency of the motor rotation. The roller frequency is a frequency at which the liquid is sucked and discharged and is calculated by a product of the frequency of the motor rotation and the number of rollers. In this way, since the roller frequency has a one-to-one correspondence with the number of motor rotations, a value obtained by converting the number of motor rotations to the roller frequency is written together as a second horizontal axis in FIG. 11.

As illustrated in FIG. 11, when the internal diameter of the pump tube 55 is smaller on the assumption of the same number of rotations, the flow rate is also smaller. Accordingly, to ensure the flow rate while the internal diameter of the pump tube 55 is small, the number of motor rotations may be increased.

In the embodiment, the flow rate is set to 4 ml/min. In the embodiment, since the liquid is intermittently ejected, a sufficient excising capacity can be ensured with the small flow rate. In order to ensure the flow rate, 30 rpm may be set in the case of ϕ 1.6 mm, 98.4 rpm may be set in the case of ϕ 0.8 mm, and 192 rpm may be set in the case of ϕ 0.5 mm.

Figure 13:
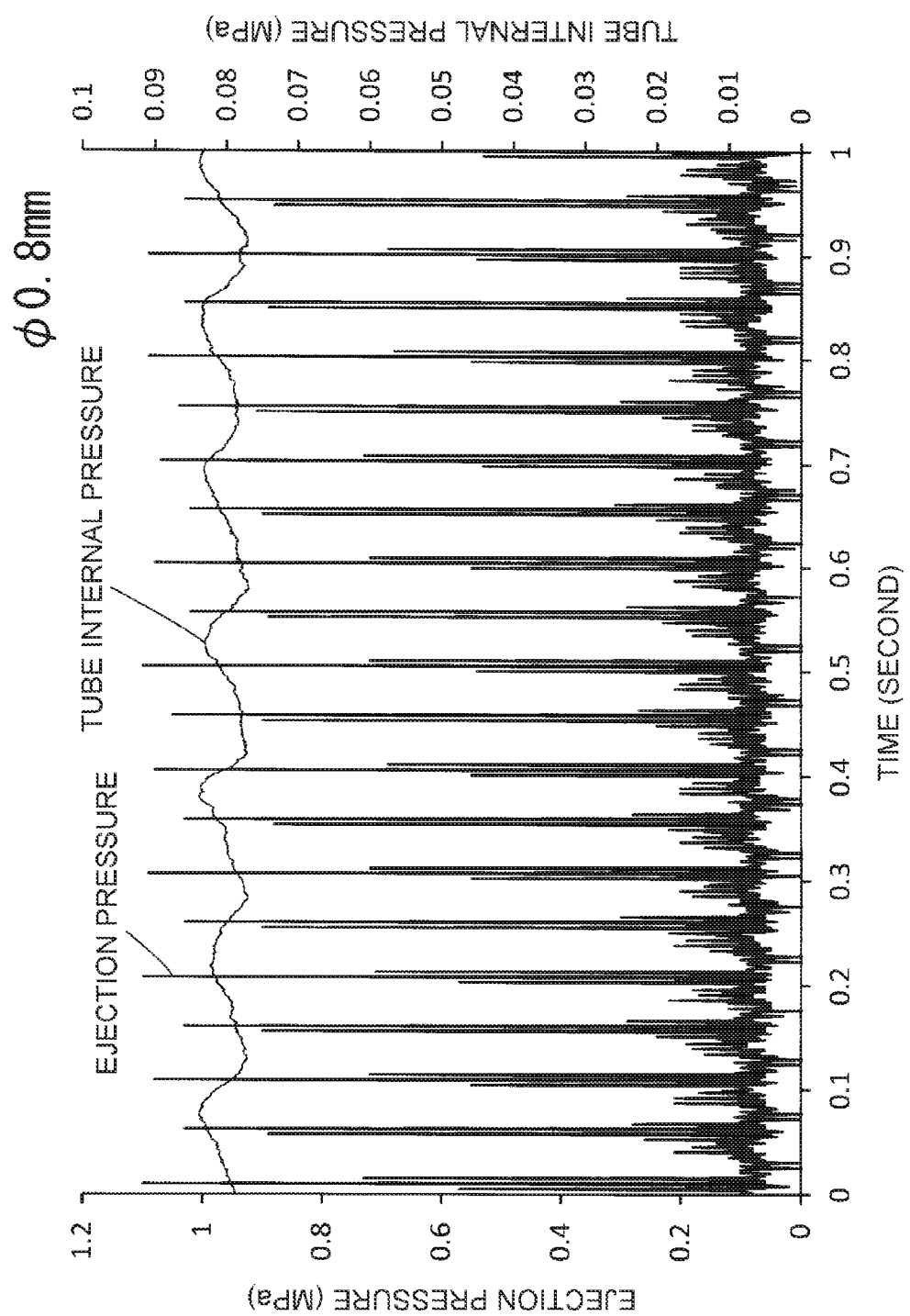
FIG. 13 is a graph illustrating an experimental result of the ejection pressure and the tube internal pressure ($\phi$ 0.8 mm).
Figure 14:
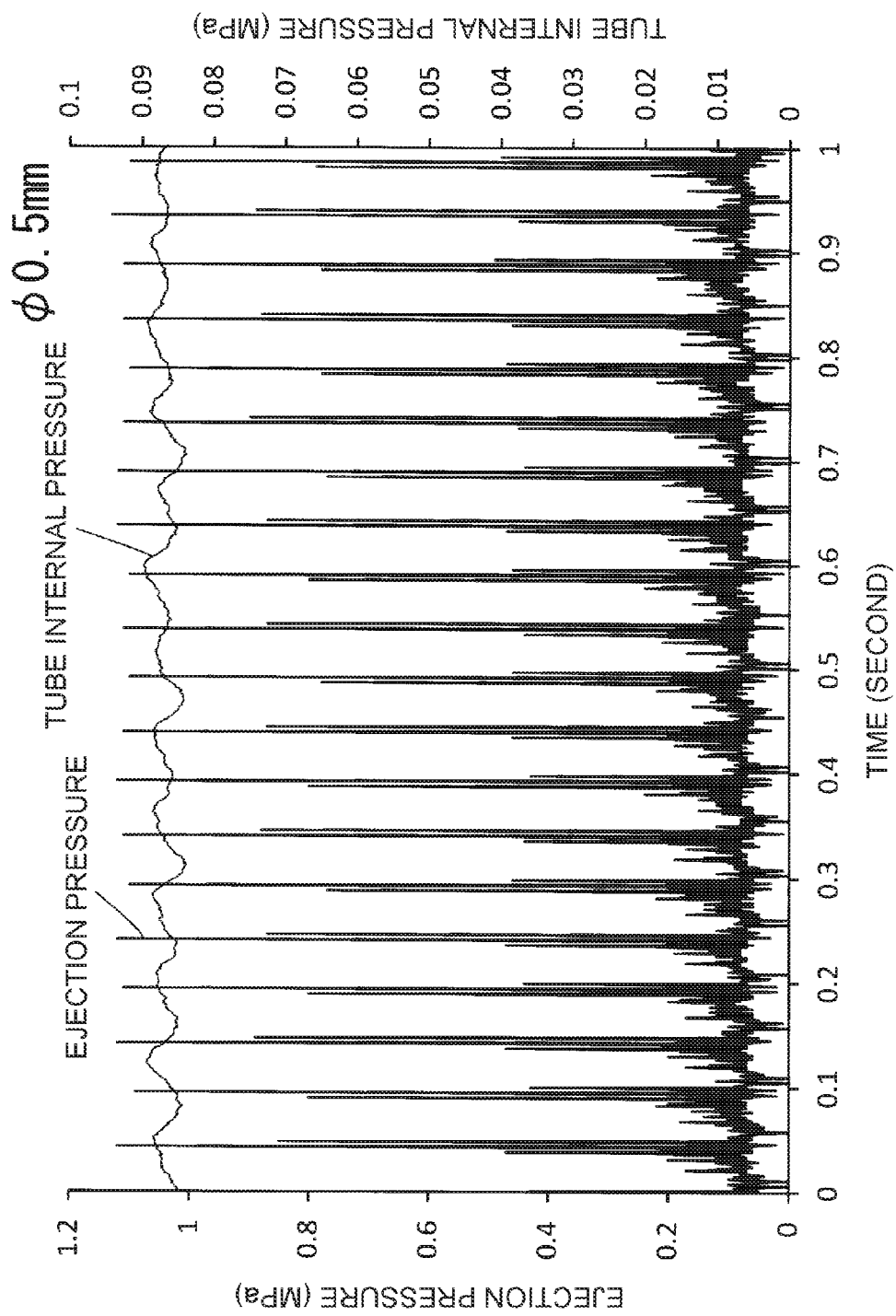
FIG. 14 is a graph illustrating an experimental result of the ejection pressure and the tube internal pressure ($\phi$ 0.5 mm).
Figure 15:
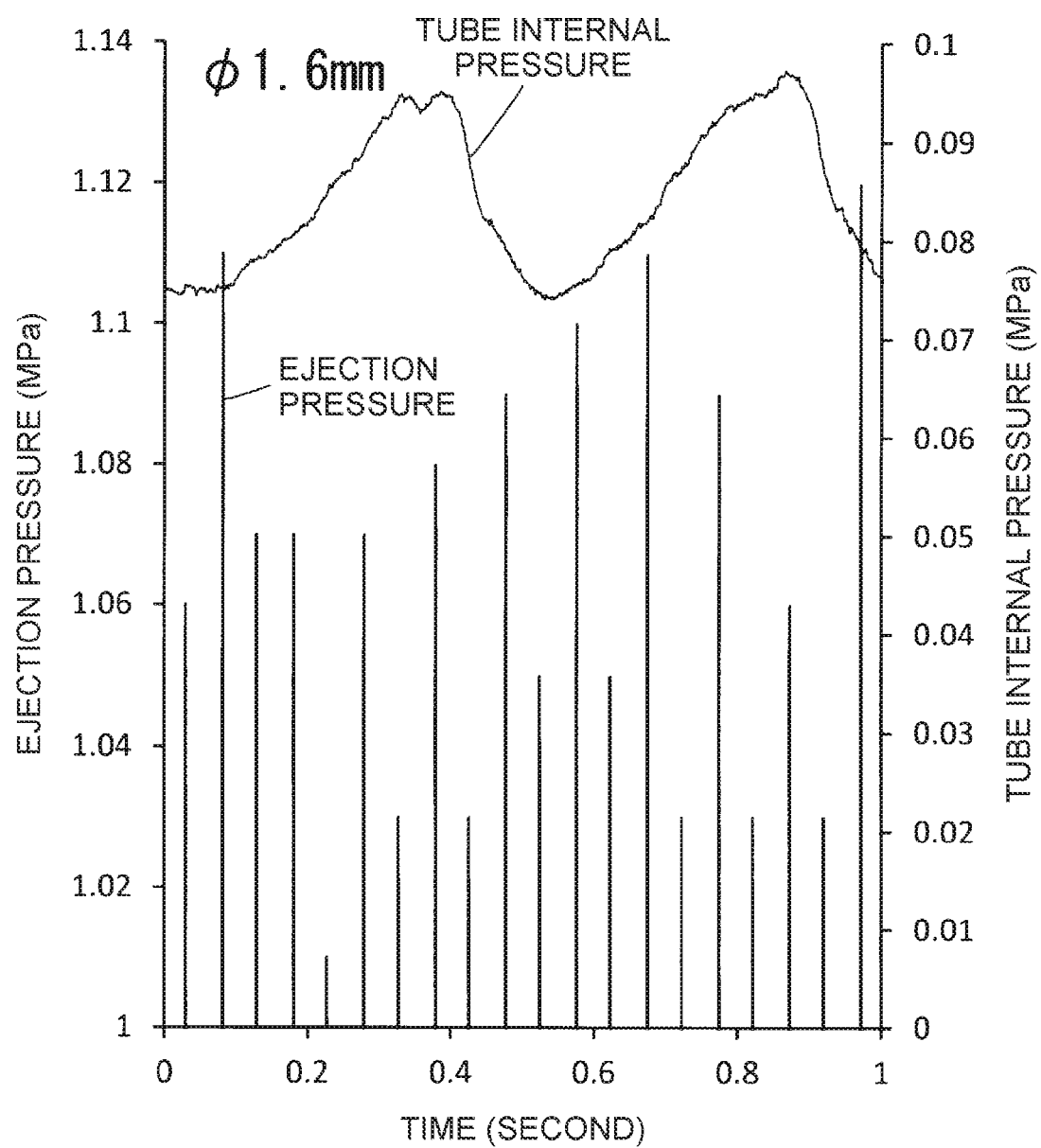
FIG. 15 is a graph illustrating an experimental result of the ejection pressure and the tube internal pressure ($\phi$ 1.6 mm).
Figure 16:
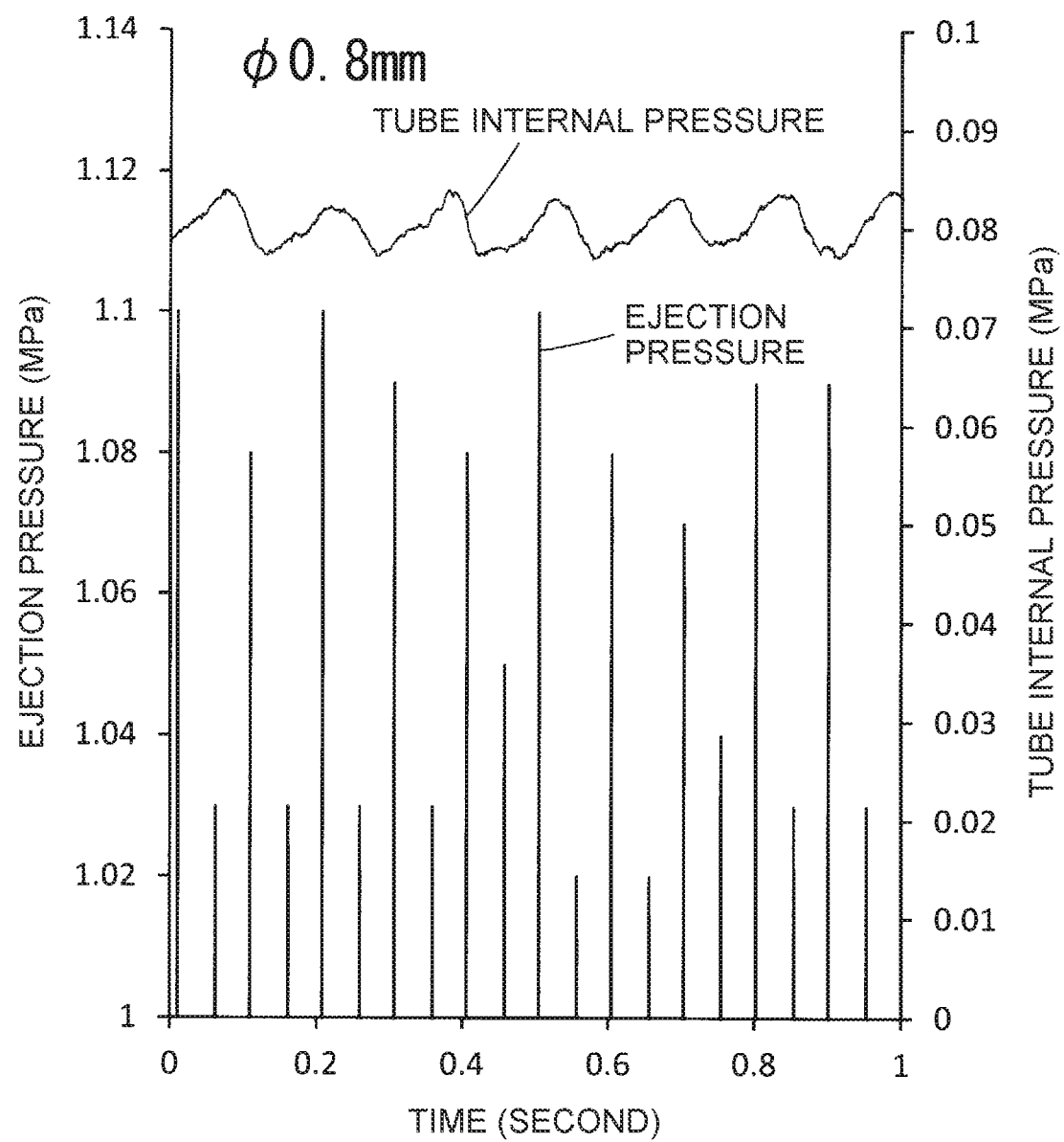
FIG. 16 is a graph illustrating an experimental result of the ejection pressure and the tube internal pressure ($\phi$ 0.8 mm).
Figure 17:
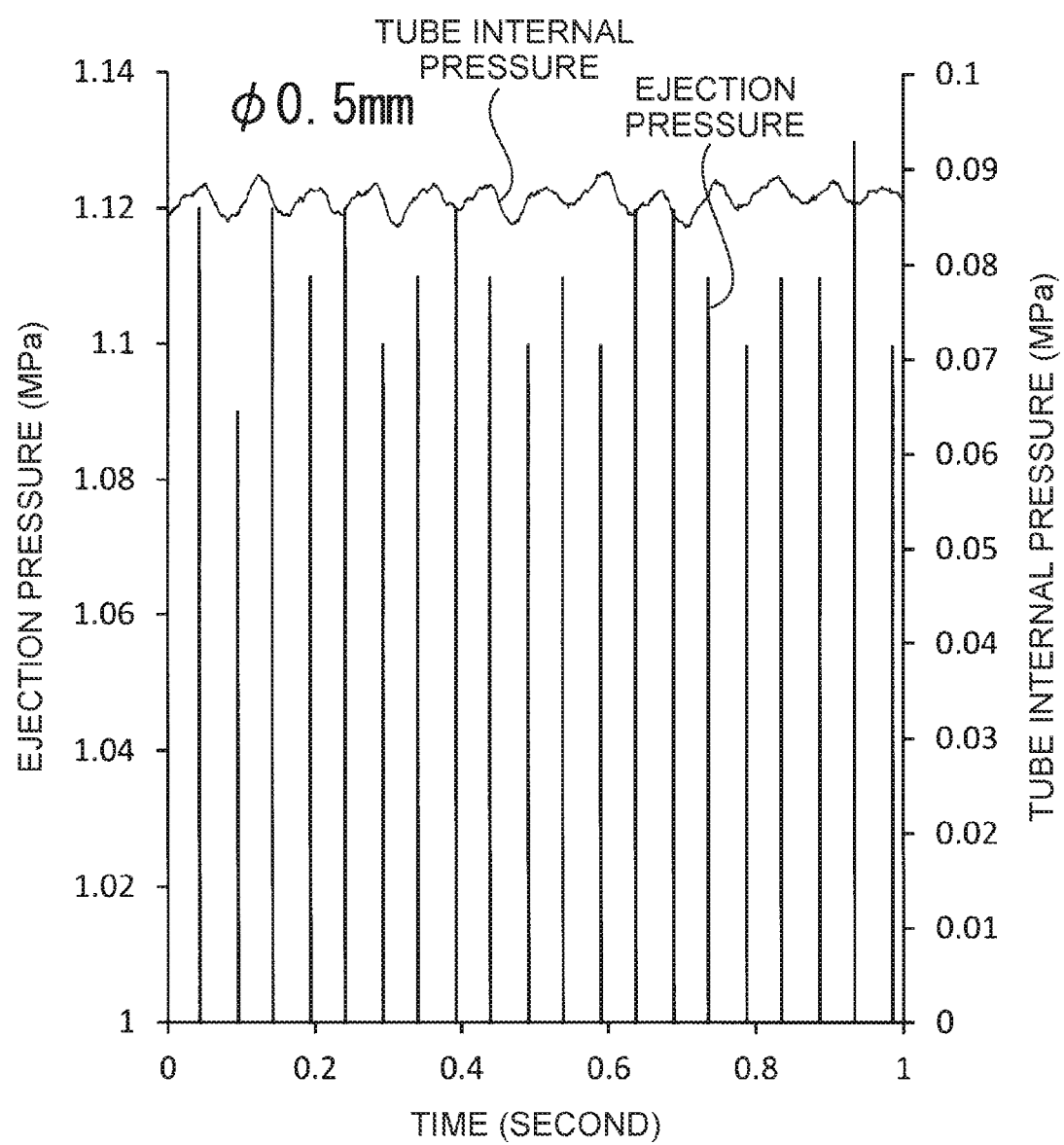
FIG. 17 is a graph illustrating an experimental result of the ejection pressure and the tube internal pressure ($\phi$ 0.5 mm).

FIGS. 12 to 17 are graphs illustrating experimental results of relations between an ejection pressure (Mpa) and a tube internal pressure (Mpa), and a time (seconds). FIGS. 15 to 17 illustrate the vicinities of peaks of the ejection pressure in an expanded manner.

The ejection pressure is a pressure of the liquid ejected from the leading end of the ejection tube 205. The tube internal pressure is a pressure on the downstream of the pump tube 55 and the upstream of the liquid chamber 240. In the embodiment, the pressure inside the fourth water feed tube 54d was measured.

Figure 12:
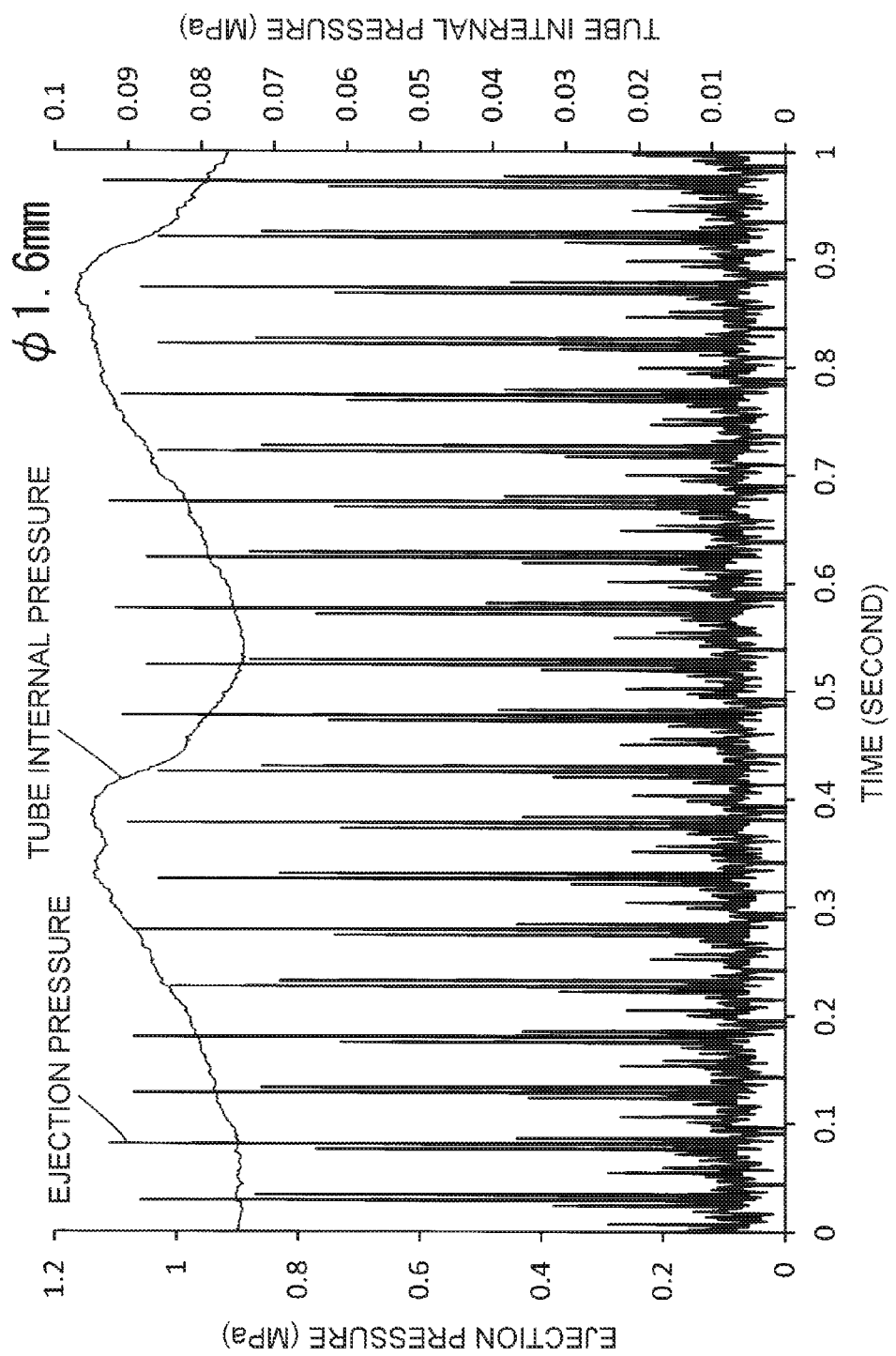
FIG. 12 is a graph illustrating an experimental result of an ejection pressure and a tube internal pressure ($\phi$ 1.6 mm).

FIGS. 12 and 15 illustrate the case in which the internal diameter of the pump tube 55 is φ 1.6 mm. FIGS. 13 and 16 illustrate the case in which the internal diameter of the pump tube 55 is φ 0.8 mm. FIGS. 14 and 17 illustrate the case in which the internal diameter of the pump tube 55 is φ 0.5 mm.

In the experiments, the frequency of the drive signal applied to the piezoelectric element 360 was set to 400 Hz and the maximum voltage was set to 35 V. In the experiments, to set the flow rate to 4 ml/min, as described above, 30 rpm was set in the case of φ 1.6 mm, 98.4 rpm was set in the case of φ 0.8 mm, and 192 rpm was set in the case of φ 0.5 mm. Since 30 rpm is 0.5 rotations per second, the roller frequency is 2.0 Hz. Since 98.4 rpm is 1.64 rotations per second, the roller frequency is 6.56 Hz. Since 192 rpm is 3.2 rotations per second, the roller frequency is 12.8 Hz.

As illustrated in FIGS. 12 and 15, when the internal diameter of the pump tube 55 is φ 1.6 mm, a variation period of the tube internal pressure is long and a variation width of the tube internal pressure is large at about ±16%. This is considered due to the fact that the internal diameter of the pump tube 55 is thick (φ 1.6 mm). That is, when the pump tube 55 is thick, a water feed amount at one time by each roller increases. Therefore, to satisfy the request for a supply flow rate, the roller frequency is lowered (2.0 Hz). As a result, the tube internal pressure considerably changes at a long period.

In addition to this, when the internal diameter of the pump tube 55 is φ 1.6 mm, the maximum value of the ejection pressure is not stabilized. This is considered due to the influence of a large variation width of the tube internal pressure.

On the other hand, as illustrated in FIGS. 13 and 16, when the internal diameter of the pump tube 55 is φ 0.8 mm, the pump tube 55 is thinner than in the case of φ 1.6 mm. Therefore, the roller frequency increases (6.56 Hz). As a result, the variation period of the tube internal pressure is shorter and the variation width decreases (about ±6%). Accordingly, when the internal diameter of the pump tube 55 is φ 0.8 mm, the maximum value of the ejection pressure is stabilized further than when the internal diameter of the pump tube 55 is φ 1.6 mm.

Further, as illustrated in FIGS. 14 and 17, when the internal diameter of the pump tube 55 is φ 0.5 mm, the variation period of the tube internal pressure is shorter and the variation width thereof is also further decreased (about ±4%) than when the internal diameter of the pump tube 55 is φ 0.8 mm. In addition to this, when the internal diameter of the pump tube 55 is φ 0.5 mm, the maximum value of the ejection pressure is stabilized further than when the internal diameter of the pump tube 55 is φ 0.8 mm.

In this way, even when a liquid supply mechanism is formed by the pump tube 55 and the tube pump 60, the variation in the tube internal pressure can be decreased and the maximum value of the ejection pressure can be stabilized. Further, in the case of the liquid supply mechanism, maintenance is simple. For the pump tube 55, a exchange work is simple and cost is low. Since the tube pump 60 does not come into contact with the liquid, the tube pump 60 can be reused.

When the internal diameter of the pump tube 55 is equal to or greater than φ 0.5 mm, for example, the internal diameter of the pump tube 55 is φ 0.5 mm or is φ 0.8 mm, the roller frequency for ensuring the same supply flow rate is smaller and the number of motor rotations of the tube pump 60 is smaller than when the internal diameter of the pump tube 55 is less than φ 0.5 mm. Therefore, when the internal diameter of the pump tube 55 is equal to or greater than φ 0.5 mm, the durability of the tube pump 60 is more preferable than when the internal diameter of the pump tube 55 is less than φ 0.5 mm. Since the pump tube 55 is disposable, no problem occurs for the durability in most cases.

Figure 18:
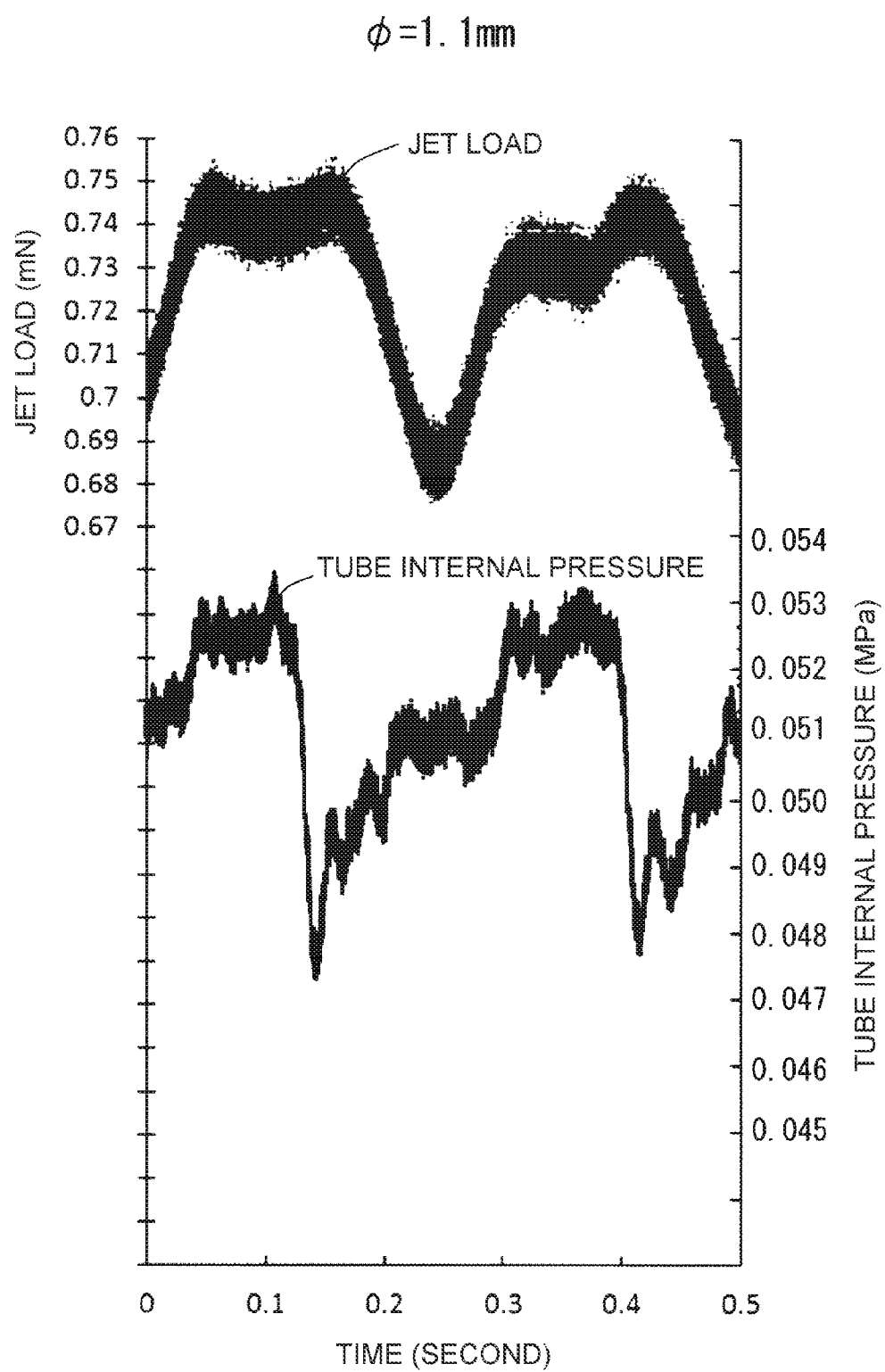
FIG. 18 is a graph illustrating an experimental result of a jet load and the tube internal pressure ($\phi$ 1.1 mm).
Figure 19:
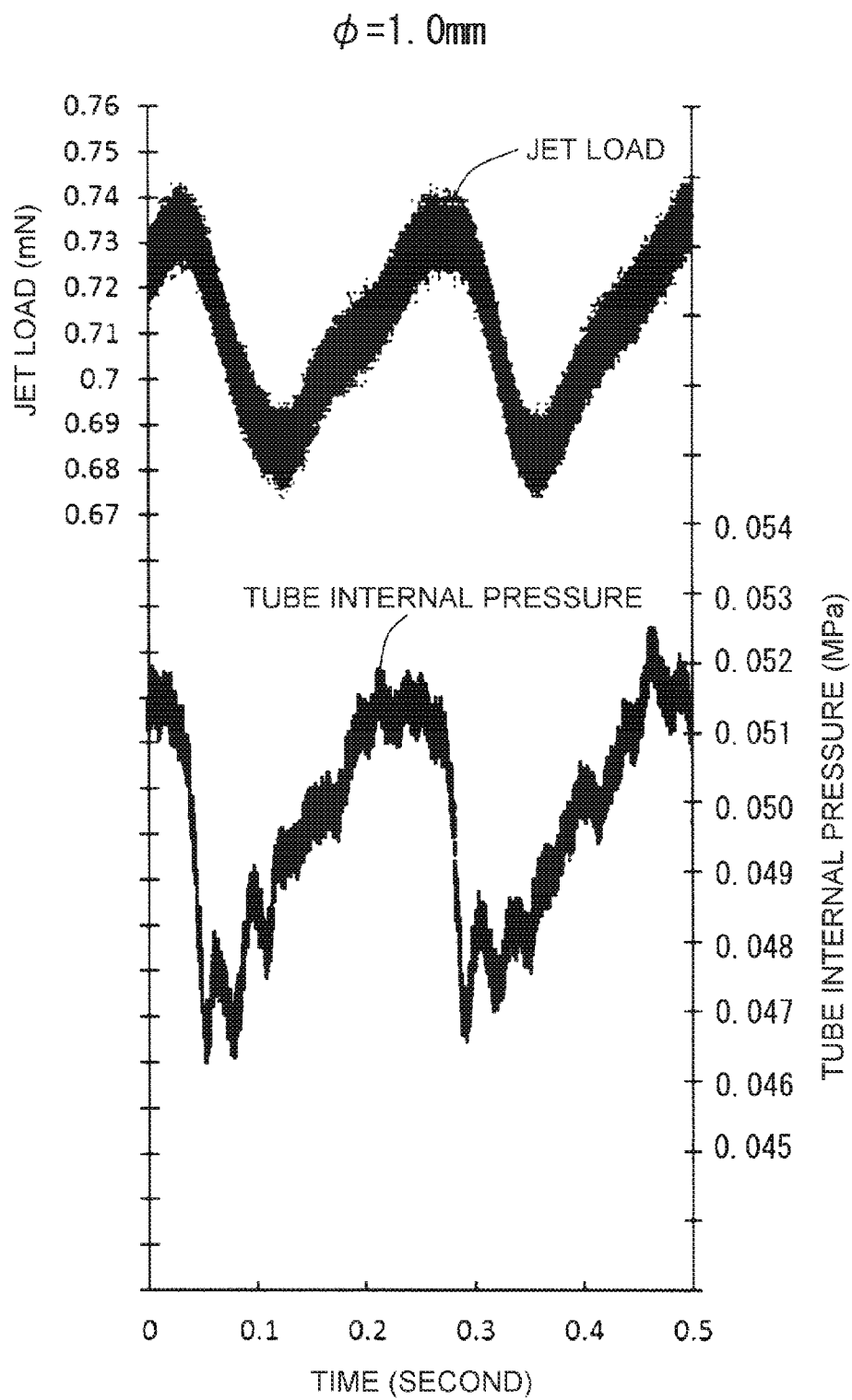
FIG. 19 is a graph illustrating an experimental result of the jet load and the tube internal pressure (ϕ 1.0 mm).
Figure 20:
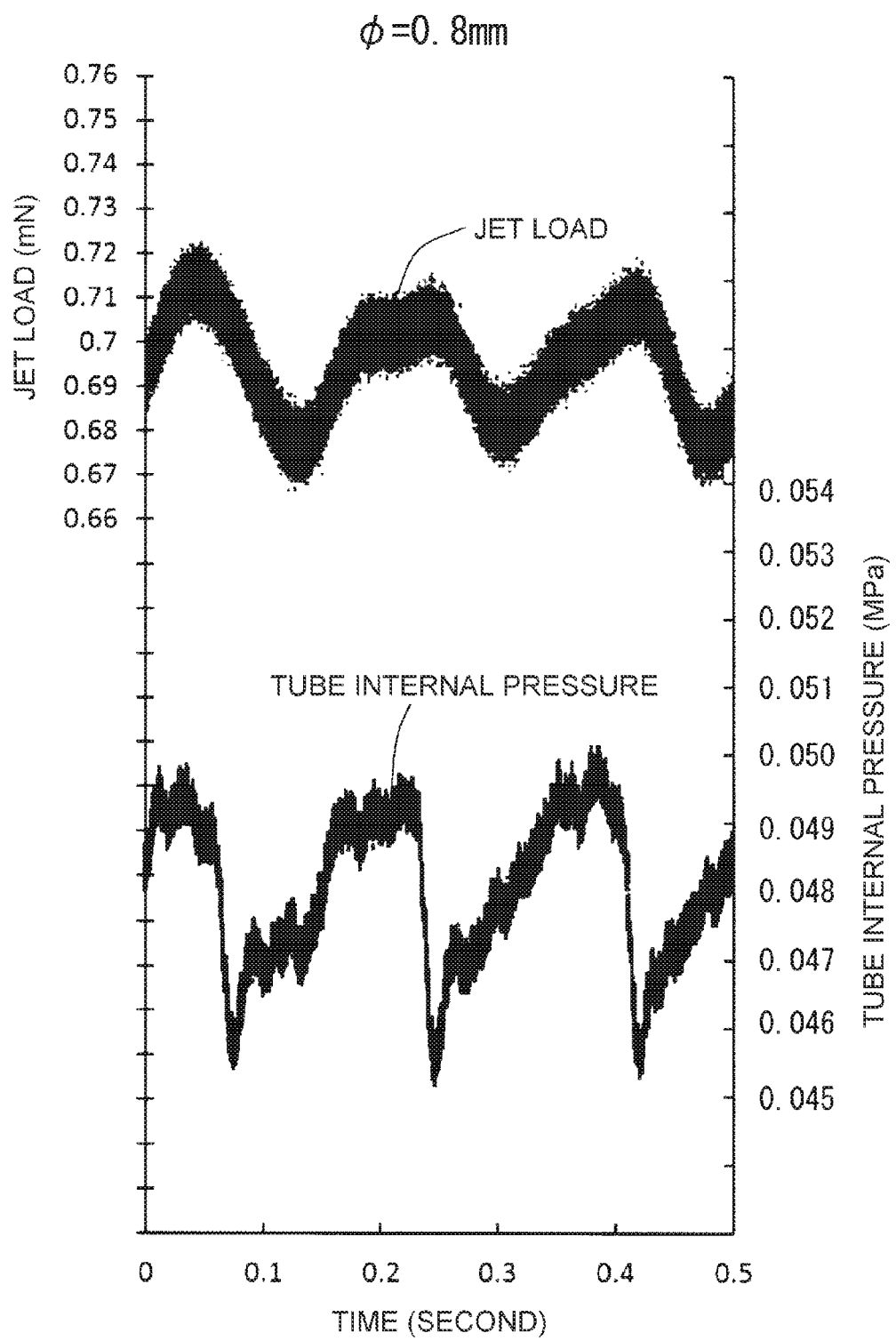
FIG. 20 is a graph illustrating an experimental result of the jet load and the tube internal pressure (ϕ 0.8 mm).

FIGS. 18 to 20 are graphs illustrating experimental results of relations between a jet load (mN) and a tube internal pressure (Mpa), and a time (seconds).

The jet load (mN) is an impact force generated by the intermittently ejected liquid. In the embodiment, a value measured by a force sensor disposed at a predetermined distance from the leading end of the nozzle 207 is defined as a jet load.

FIG. 18 illustrates a case in which the internal diameter of the pump tube 55 is φ 1.1 mm (hereinafter, when the numerical value of the internal diameter is shown, the internal diameter of the pump tube 55" is omitted), FIG. 19 illustrates a case of φ 1.0 mm, and FIG. 20 illustrates a case of φ 0.8 mm.

The number of rotations of the tube pump 60 was set to 55.2 rpm in the case of φ 1.1 mm, was set to 57.6 rpm in the case of φ 1.0 mm, and was set to 86.4 rpm in the case of φ 0.8 mm. When the number of rotations is converted into the roller frequency, the roller frequency is 3.68 Hz in the case of φ 1.1 mm, is 3.84 Hz in the case of φ 1.0 mm, and is 5.76 Hz in the case of φ 0.8 mm.

The results obtained by statistically processing data of the tube internal pressures obtained in the experiments are as follows. In the subsequent statistical process, data of 0.5 seconds to 1.0 second is also included in addition to data of 0 seconds to 0.5 seconds shown in the graphs.

In the case of φ 1.1 mm, an average value was $51.0 \times 10^{-3}$ Mpa, a standard deviation was $1.4 \times 10^{-3}$ Mpa, a maximum value was $53.4 \times 10^{-3}$ Mpa, and a minimum value was $47.1 \times 10^{-3}$ Mpa.

In the case of φ 1.0 mm, an average value was $49.7 \times 10^{-3}$ Mpa, a standard deviation was $1.5 \times 10^{-3}$ Mpa, a maximum value was $52.9 \times 10^{-3}$ Mpa, and a minimum value was $46.2 \times 10^{-3}$ Mpa.

In the case of φ 0.8 mm, an average value was $48.1 \times 10^{-3}$ Mpa, a standard deviation was $1.1 \times 10^{-3}$ Mpa, a maximum value was $50.2 \times 10^{-3}$ Mpa, and a minimum value was $45.1 \times 10^{-3}$ Mpa.

As described above, the standard deviation of the tube internal pressure is smaller in the case of φ 0.8 mm than in the case of φ 1.0 mm and the case of φ 1.1 mm. Accordingly, φ 0.8 mm is more preferable than φ 1.0 mm and φ 1.1 mm. Further, 5.76 Hz which is the roller frequency in the case of φ 0.8 mm is more preferable than 3.68 Hz in the case of φ 1.1 mm and 3.84 Hz in the case of φ 1.0 mm.

The results obtained by statistically processing the data of the jet load obtained in the experiments are as follows.

In the case of φ 1.1 mm, an average value was 0.72 mN, a standard deviation was 0.019 mN, a maximum value was 0.76 mN, and a minimum value was 0.67 mN.

In the case of φ 1.0 mm, an average value was 0.71 mN, a standard deviation was 0.017 mN, a maximum value was 0.75 mN, and a minimum value was 0.66 mN.

In the case of φ 0.8 mm, an average value was 0.70 mN, a standard deviation was 0.012 mN, a maximum value was 0.72 mN, and a minimum value was 0.67 mN.

As described above, the standard deviation of the jet load in the case of φ 1.0 mm is less than that in the case of φ 1.1 mm. That is, the jet load is stabilized. Accordingly, φ 1.0 mm is more preferable than ϕ 1.1 mm. Further, 3.84 Hz which is the roller frequency in the case of ϕ 1.0 mm is more preferable than 3.68 Hz in the case of ϕ 1.1 mm.

As described above, the standard deviation of the jet load in the case of ϕ 0.8 mm is less than that in the case of ϕ 1.0 mm. Accordingly, ϕ 0.8 mm is more preferable than ϕ 1.0 mm. Further, 5.76 Hz which is the roller frequency in the case of ϕ 0.8 mm is more preferable than 3.84 Hz in the case of ϕ 1.0 mm.

The invention is not limited to the embodiments, the examples, and the modification examples of the present specification, and can be realized in various configurations in the scope of the invention without departing from the gist of the invention. For example, technical features of the embodiments, the examples, and the modification examples corresponding to technical features of the aspects described in Summary of the invention can be replaced or combined to resolve some or all of the above-described problems or achieve some or all of the above-described advantages. When the technical features are not described as requisites in the present specification, the technical features can be appropriately cancelled. For example, the following can be exemplified.

The internal diameter of the pump tube may be thinner than ϕ 0.5 mm.

The roller frequency of the tube pump may be greater than 12.8 Hz, may be less than 6.56 Hz, or may be less than 3.84 Hz.

A supply flow rate by the tube pump may be, for example, equal to or greater than 3 ml/min and equal to or less than 10 ml/min. Alternatively, the flow rate may be any other value.

The wall thickness of the pump tube may be thicker than 1.6 mm or may be thinner than 1.6 mm.

The number of rollers included in the tube pump may be, for example, 3 other than 4. When the number of rollers is changed, the number of motor rotations may be adjusted to maintain the roller frequencies.

The nozzle unit and the actuator unit may be integrated.

The nozzle unit may be used a plurality of times by performing a sterilization treatment.

The liquid to be ejected may be pure water or a liquid medicine.

The liquid ejection device may be used for a device other than a medical apparatus.

For example, the liquid ejection device may be used for a cleaning device which removes dirt using an ejected liquid or may be used for a drawing device which draws a line or the like using an ejected liquid.

In the embodiment, the configuration in which the piezoelectric element is used as an actuator has been adopted, but a configuration in which a liquid is ejected using an optical maser may be adopted or a configuration in which a liquid is ejected by pressurizing the liquid by a pump or the like may be adopted. The configuration in which a liquid is ejected using an optical maser is a configuration in which an optical maser is emitted to a liquid to generate bubbles and a pressure increase of the liquid occurring by the generation of the bubbles is used.

In the embodiment, the configuration in which the liquid is intermittently ejected has been adopted, but a configuration having a function of continuously ejecting a liquid may be adopted. For example, a configuration in which intermittent ejection and continuous ejection may be distinguished to be used may be adopted. To perform the continuous ejection using the hardware configuration of the embodiment, only the tube pump may be driven when the driving of the actuator stops or deteriorates. In the case of this configuration, the intermittent ejection may be performed for excising and the continuous ejection may be performed for cleaning.

Alternatively, a configuration in which only continuous ejection can be performed may be adopted. In the case of this configuration, excising may be performed through the continuous ejection.

The entire disclosure of Japanese Patent Application No. 2015-054197 filed Mar. 18, 2015 and No. 2015-235278 filed Dec. 2, 2015 are expressly incorporated by reference herein.

What is claimed is:

1. A liquid supply device comprising:
   a pump tube that supplies a liquid to a handpiece intermittently ejecting the liquid; and
   a tube pump that passes the pump tube to supply the liquid,
   wherein an internal diameter of the pump tube is equal to or less than ϕ 1.0 mm.

2. The liquid supply device according to claim 1,
   wherein the internal diameter of the pump tube is equal to or less than ϕ 0.8 mm.

3. The liquid supply device according to claim 1,
   wherein the internal diameter of the pump tube is equal to or less than ϕ 0.5 mm.

4. The liquid supply device according to claim 1,
   wherein the internal diameter of the pump tube is equal to or greater than ϕ 0.5 mm.

5. The liquid supply device according to claim 1,
   wherein a roller frequency of the tube pump is equal to or greater than 3.84 Hz.

6. The liquid supply device according to claim 5,
   wherein the roller frequency of the tube pump is equal to or greater than 6.56 Hz.

7. The liquid supply device according to claim 6,
   wherein the roller frequency of the tube pump is equal to or greater than 12.8 Hz.

8. The liquid supply device according to claim 1,
   wherein a wall thickness of the pump tube is equal to or greater than 1.6 mm.

9. The liquid supply device according to claim 1,
   wherein the handpiece is a surgical excising mechanism, and
   wherein a supply flow rate by the tube pump is equal to or greater than 3 ml/min and equal to or less than 10 ml/min.

10. A liquid ejection device comprising:
    the handpiece and the liquid supply device according to claim 1.

11. A liquid ejection device comprising:
    the handpiece and the liquid supply device according to claim 2.

12. A liquid ejection device comprising:
    the handpiece and the liquid supply device according to claim 3.

13. A liquid ejection device comprising:
    the handpiece and the liquid supply device according to claim 4.

14. A liquid ejection device comprising:
    the handpiece and the liquid supply device according to claim 5.

15. A liquid ejection device comprising:
    the handpiece and the liquid supply device according to claim 6.

16. A liquid ejection device comprising:
    the handpiece and the liquid supply device according to claim 7.

17. A liquid ejection device comprising:
the handpiece and the liquid supply device according to claim 8.
18. A liquid ejection device comprising:
the handpiece and the liquid supply device according to claim 9.

* * * * *